United States Patent
Wagstaff

(10) Patent No.: US 10,035,010 B1
(45) Date of Patent: Jul. 31, 2018

(54) SYSTEMS AND METHODS FOR DRUG DELIVERY

(71) Applicant: Carydean Enterprises LLC, Milford, NJ (US)

(72) Inventor: Dean Henry Wagstaff, Milford, NJ (US)

(73) Assignee: CARYDEAN ENTERPRISES LLC, Milford, NJ (US)

( * ) Notice: Subject to any disclaimer, the term of this patent is extended or adjusted under 35 U.S.C. 154(b) by 0 days.

(21) Appl. No.: 15/718,017

(22) Filed: Sep. 28, 2017

(51) Int. Cl.
*A61M 35/00* (2006.01)
*A61M 5/172* (2006.01)
(Continued)

(52) U.S. Cl.
CPC ........ *A61M 37/0092* (2013.01); *A61M 35/00* (2013.01); *A61B 5/681* (2013.01);
(Continued)

(58) Field of Classification Search
CPC ........ A61M 2230/005; A61M 5/14244; A61M 5/14248; A61M 5/172; A61M 5/1723;
(Continued)

(56) References Cited

U.S. PATENT DOCUMENTS 6,002,961 A 12/1999 Mitragotri et al.
6,980,855 B2 * 12/2005 Cho ................. A61M 37/0015
604/20

(Continued)

FOREIGN PATENT DOCUMENTS

CN 103245776 A 8/2013
CN 204013674 U 12/2014
(Continued)

OTHER PUBLICATIONS

Pattnaik et al., "Alternate Glucometer Bio-sensor Model Based on Ultrasonic MEMS Transceivers", Proceedings of the 2013 COMSOL conference, 2013, retrieved on Jul. 10, 2017 from https://www.comsol.com/paper/download/182793/pattnaik_paper.pdf, 6 Pages.

(Continued)

*Primary Examiner* — Quynh-Nhu H Vu
(74) *Attorney, Agent, or Firm* — Maldjian Law Group LLC

(57) ABSTRACT

A wearable device for monitoring the body parameters of an individual and for delivering a drug and/or therapeutic agent. The device comprises a processing unit and a drug delivery unit. The processing unit comprises a sensor to determine body parameters of a user; a reservoir to store the drug; a processor to receive signals indicative of the body parameters from the sensor and determine a quantity of the drug to be delivered from the reservoir based on the body parameters; and a signal generator to generate electrical signals based on control instructions received from the processor. The drug delivery unit comprises a chamber to receive the determined quantity of the drug from the reservoir and a transducer connected to the chamber, wherein the transducer transdermally delivers the drug from the chamber to skin based on an electrical signal received from the signal generator.

20 Claims, 32 Drawing Sheets

(51) Int. Cl.
*A61M 37/00* (2006.01)
*A61B 5/00* (2006.01)

(52) U.S. Cl.
CPC .............. *A61M 2037/0007* (2013.01); *A61M 2205/0211* (2013.01); *A61M 2205/0244* (2013.01); *A61M 2205/3303* (2013.01); *A61M 2205/3569* (2013.01); *A61M 2205/50* (2013.01); *A61M 2205/502* (2013.01); *A61M 2205/52* (2013.01); *A61M 2205/8206* (2013.01); *A61M 2230/201* (2013.01)

(58) Field of Classification Search
CPC .. A61M 35/003; A61M 1/30; A61M 37/0015; A61M 2037/0023; A61M 37/0092; A61M 35/00; A61M 2205/50; A61M 2205/8206; A61M 2205/52; A61M 2230/201; A61M 2205/3569; A61M 2205/0244; A61M 2205/0211; A61M 2037/0007; A61M 2205/3303; A61B 5/681
See application file for complete search history.

(56) References Cited

U.S. PATENT DOCUMENTS

| | | | |
|---|---|---|---|
| 7,163,511 | B2 | 1/2007 | Conn et al. |
| 8,029,443 | B2 | 10/2011 | Goodnow |
| 8,077,042 | B2 | 12/2011 | Peeters |
| 8,135,450 | B2 | 3/2012 | Esenaliev et al. |
| 8,229,535 | B2 * | 7/2012 | Mensinger .......... A61B 5/7445 600/345 |
| 8,235,897 | B2 | 8/2012 | Gal et al. |
| 8,268,243 | B2 | 9/2012 | Drucker et al. |
| 8,531,824 | B2 | 9/2013 | Rayner |
| 8,591,410 | B2 | 11/2013 | Taub et al. |
| 8,597,570 | B2 | 12/2013 | Terashima et al. |
| 8,684,922 | B2 | 4/2014 | Tran |
| 8,737,971 | B2 | 5/2014 | Van Rooyen et al. |
| 8,843,184 | B2 | 9/2014 | Kim et al. |
| 8,870,766 | B2 | 10/2014 | Stivoric et al. |
| 8,926,585 | B2 | 1/2015 | Brauker et al. |
| 9,089,292 | B2 | 7/2015 | Roy et al. |
| 9,125,549 | B2 | 9/2015 | Weintraub et al. |
| 9,241,551 | B2 | 1/2016 | Lawson et al. |
| 9,264,088 | B2 | 2/2016 | Wojcik et al. |
| 9,332,334 | B2 | 5/2016 | Chardon et al. |
| 9,374,788 | B2 | 6/2016 | Singamsetti et al. |
| 9,398,127 | B2 | 7/2016 | Ikemoto et al. |
| 9,406,913 | B2 | 8/2016 | Huang et al. |
| 9,495,375 | B2 | 11/2016 | Huang et al. |
| 9,632,056 | B2 | 4/2017 | Iyengar et al. |
| 9,642,563 | B2 | 5/2017 | Crawford et al. |
| 9,713,440 | B2 | 7/2017 | Hurd et al. |
| 9,774,713 | B2 | 9/2017 | Guerdrum et al. |
| 9,807,211 | B2 | 10/2017 | Guerdrum et al. |
| 2004/0087916 | A1 * | 5/2004 | Pickup .................. A01K 11/005 604/305 |
| 2005/0038377 | A1 | 2/2005 | Redding, Jr. |
| 2008/0166791 | A1 | 7/2008 | Kim et al. |
| 2009/0186264 | A1 | 7/2009 | Huang |
| 2010/0000862 | A1 | 1/2010 | Rao |
| 2010/0041156 | A1 | 2/2010 | Brenneman et al. |
| 2010/0279418 | A1 | 11/2010 | Larson et al. |
| 2010/0298764 | A1 | 11/2010 | Yodfat et al. |
| 2011/0154889 | A1 | 6/2011 | Stafford et al. |
| 2011/0163881 | A1 | 7/2011 | Halff et al. |
| 2012/0059237 | A1 | 3/2012 | Amir et al. |
| 2012/0063066 | A1 | 3/2012 | Floit |
| 2012/0100601 | A1 | 4/2012 | Simmons et al. |
| 2012/0149245 | A1 | 6/2012 | Ralston et al. |
| 2012/0168336 | A1 | 7/2012 | Schmidt et al. |
| 2012/0220220 | A1 | 8/2012 | Deluca et al. |
| 2012/0330556 | A1 | 12/2012 | Shaanan et al. |
| 2013/0053652 | A1 | 2/2013 | Cooner |
| 2014/0005499 | A1 | 1/2014 | Catt et al. |
| 2014/0018655 | A1 | 1/2014 | Abulhaj et al. |
| 2014/0035511 | A1 | 2/2014 | Ferber et al. |
| 2014/0072189 | A1 | 3/2014 | Jena et al. |
| 2014/0168885 | A1 | 6/2014 | Williams |
| 2014/0170761 | A1 | 6/2014 | Crawford et al. |
| 2014/0321048 | A1 | 10/2014 | Kupferstein |
| 2014/0326636 | A1 | 11/2014 | Baschnagel |
| 2014/0364711 | A1 | 12/2014 | Ismail et al. |
| 2015/0112170 | A1 | 4/2015 | Amerson, III et al. |
| 2015/0246179 | A1 | 9/2015 | Zur et al. |
| 2015/0381226 | A1 | 12/2015 | Mogol |
| 2016/0072933 | A1 | 3/2016 | Cox, III |
| 2016/0118861 | A1 | 4/2016 | Gabriel et al. |
| 2016/0141910 | A1 | 5/2016 | Klawon et al. |
| 2016/0148535 | A1 | 5/2016 | Ashby |
| 2016/0308569 | A1 | 10/2016 | Wei |
| 2016/0315652 | A1 | 10/2016 | Tabatabai et al. |
| 2016/0331315 | A1 | 11/2016 | Carter et al. |
| 2016/0361032 | A1 | 12/2016 | Carter et al. |
| 2016/0367202 | A1 | 12/2016 | Carter et al. |
| 2016/0374599 | A1 | 12/2016 | Frattarola |
| 2017/0005683 | A1 | 1/2017 | Yang et al. |
| 2017/0095189 | A1 | 4/2017 | Ralston et al. |
| 2017/0099377 | A1 | 4/2017 | Moran et al. |

FOREIGN PATENT DOCUMENTS

| | | |
|---|---|---|
| CN | 204389504 U | 6/2015 |
| WO | 2002005702 A2 | 1/2002 |
| WO | 2015138964 A1 | 9/2015 |
| WO | 2016055671 A1 | 4/2016 |
| WO | 2016080911 A1 | 5/2016 |
| WO | 2016169459 A1 | 10/2016 |

OTHER PUBLICATIONS

Yilmaz et al., "Detecting Vital Signs with Wearable Wireless Sensors", Sensors, vol. 10, No. 12, Dec. 2, 2010, retrieved on Jul. 10, 2017 from https://www.ncbi.nlm.nih.gov/pmc/articles/PMC3231103/pdf/sensors-10-10837.pdf, pp. 10837-10862.

Mayo, "Report: Tim Cook Testing Wearable Blood Sugar Tracker on Apple's Campus, Connected to Apple Watch", May 18, 2017, retrieved on Jul. 10, 2017 from https://9to5mac.com/2017/05/18/report-tim-cook-testing-wearable-blood-sugar-tracker-on-apples-campus-connected-to-apple-watch/, 12 Pages.

Medhelp, "Sugar Sense—Diabetes App, Blood Sugar Control, and Carb Counter", Jun. 26, 2017, retrieved on Jul. 10, 2017 from https://itunes.apple.com/in/app/sugar-sense-diabetes-app-blood/id880725347?mt=8, 4 Pages.

Lee et al., "Wearable/Disposable Sweat-Based Glucose Monitoring Device with Multistage Transdermal Drug Delivery Module", Bioengineering, Science Advances, vol. 3, No. 3, Mar. 8, 2017, retrieved on Jul. 10, 2017 from http://advances.sciencemag.org/content/advances/3/3/e1601314.full.pdf, 8 Pages.

Gartenberg, "You Can Now Spend Money on the First iPhone 7 Headphone Jack Case", The Verge, Sep. 29, 2016, retrieved on Nov. 25, 2016 from https://www.theverge.com/circuitbreaker/2016/9/29/13105292/fuze-phone-7-battery-pack-headphone-jack-case, 8 Pages.

Fox, "Daptr Brings the Headphone Jack to the iPhone 7", Hypebeast, Sep. 19, 2016, retrieved on Nov. 25, 2016 from https://hypebeast.com/2016/9/daptr-apple-iphone-7-case-headphone-jack, 14 Pages.

Otter Products, "PolarPro PowerPack _OtterBox", retrieved on Nov. 25, 2016 from http://www.otterbox.com/en-us/polarpro/powerpack/plpr-powerpack.html, 3 Pages.

Sandisk, "Ixpand Flash Drive", retrieved on Nov. 24, 2016 from https://www.sandisk.in/home/mobile-device-storage/ixpand, 9 Pages.

Apple Inc., "iPhone Lightning Dock", retrieved on Nov. 25, 2016 from https://www.apple.com/shop/product/MNN62AM/A/iphone-lightning-dock-black?afid=p231%7Ccamref 103A11OOIaKZ&cid=AOS-US-AFF-PHG, 3 Pages.

(56) References Cited

OTHER PUBLICATIONS

Hoskins, "AkibaH and the GluCase: Building a Glucose Meter and Supplies into Your Smartphone Case", Diabetes Mine, Healthline, Sep. 28, 2015, 6 Pages.
Health, "iHealth Align", retrieved on May 11, 2016, 3 Pages.
Saenz, "Testing Your Blood Sugar with Your iPhone", SingularityHub, Sep. 22, 2010, retrieved on May 11, 2016 from https://singularityhub.com/2010/09/22/testing-your-blood-sugar-with-your-iphone/, 3 Pages.

* cited by examiner

1800

1800
1812

1806

SYSTEMS AND METHODS FOR DRUG DELIVERY

FIELD OF THE INVENTION

Embodiments of the present invention generally relate to systems and methods for drug delivery. In particular, the present invention relates to a wearable device for the monitoring of the body parameters of an individual and for providing a drug delivery system and method based on the data received.

BACKGROUND

Lifestyle changes have contributed to health concerns worldwide. Continuous monitoring of an individual's body parameters, including, but not limited to, vital signs and blood data, is important to prevent health issues arising due to lifestyle changes. Various devices have been introduced that provide monitoring services to a user. These include glucometers, cardio-monitoring devices, fitness trackers etc. As a result of the body parameter data received, a drug or a therapeutic agent may be administered to a patient and or individual. For the purposes of clarity, the terms patient and individual are synonymous as are the terms drug and therapeutic agent and may be used interchangeably.

Drug delivery devices are used for the delivery of a drug or therapeutic agent to a patient. Certain drugs are traditionally administered into the bloodstream of a patient by piercing the skin of a patient using a syringe or through the use of a pump which is often worn on the body of an individual.

Examples of prevalent medical issues include diabetes. Patients suffering from diabetes are generally required to regularly monitor and manage their blood glucose levels. Various glucose meters are well known in the medical industry to measure and monitor one's blood glucose levels. Typically, a pricking needle or a lancet is used to prick the skin of a patient. A droplet of blood is placed onto a sensor strip that is placed in an analyte sensing device. A chemical reaction occurs in the sensor strip and data, i.e., blood glucose level, is generated, which is then displayed on the measuring device indicating the blood glucose level of the user. Moreover, in some glucose measuring devices, the data can also be sent to other devices, such as a computer or a cell phone. Such invasive monitoring techniques may be inconvenient to patients. Further, insulin is to be injected if the glucose levels are not to an optimum level. Typically, insulin is injected through an invasive method, such as a syringe mechanism. In other instances, insulin is administered through the use of a pump which is often worn by an individual twenty-four (24) hours a day to ensure adequate dosing.

Invasive methods of administering a drug can be cumbersome and may require some expertise on the part of the user. In some cases, patients may have to visit a medical facility to take insulin shots from a professional medical practitioner.

Therefore, there is a need for a device that provides non-invasive monitoring and drug delivery.

SUMMARY

Embodiments in accordance with the present invention provide a wearable non-invasive device to monitor an individual's body parameters and for drug delivery. The wearable non-invasive device delivers a stored drug or a therapeutic agent transdermally through the skin of a user.

Embodiments in accordance with the present invention provide a wearable device for drug delivery. The wearable device delivers a drug based on determination of one or more body parameters of the user.

Embodiments in accordance with the present invention provide a wearable device for drug delivery, the wearable device comprising at least one transducer, one or more biosensors for determining one or more body parameters, a processor for analyzing data obtained from the one or more biosensors, a screen for displaying the determined body parameters, and a power source for providing power to various components of the wearable device. All the components of the wearable device are disposed on an adjustable band or strap.

Some embodiments of the present invention are directed to a wearable device for delivering a drug. The wearable device comprises a processing unit and a drug delivery unit. The processing unit comprises at least one sensor, wherein the at least one sensor is configured to determine one or more body parameters of a user; a reservoir containing a quantity of the drug; a processor communicably coupled to the at least one sensor, wherein the processor is configured to receive one or more signals indicative of the one or more body parameters from the at least one sensor and determine a quantity of the drug to be delivered from the reservoir based on the one or more body parameters; and a signal generator configured to generate electrical signals based on control instructions received from the processor. The drug delivery unit comprises a chamber configured to receive the determined quantity of the drug from the reservoir and a transducer connected to the chamber, wherein the transducer is configured to transdermally deliver the drug from the chamber to skin of the user based on an electrical signal received from the signal generator.

Other embodiments are directed to a wearable device for delivering a drug, the wearable device comprising a band configured to be detachably attached to a user, a processing unit disposed on the band, and a drug delivery unit disposed on the band and connected to the processing unit. The processing unit comprises at least one sensor, wherein the at least one sensor is configured to determine one or more body parameters of a user; a reservoir containing a drug; a processor communicably coupled to the at least one sensor, wherein the processor is configured to receive one or more signals indicative of the one or more body parameters from the at least one sensor and determine a quantity of the drug to be delivered from the reservoir based on the one or more body parameters; and a signal generator configured to generate electrical signals based on control instructions received from the processor. The drug delivery unit comprises a chamber configured to receive the determined quantity of the drug from the reservoir and a transducer connected to the chamber, wherein the transducer is configured to transdermally deliver the drug from the chamber to skin of the user based on an electrical signal received from the signal generator.

Yet other embodiments are directed to a wearable device for delivering a drug, the wearable device comprising a band worn on a wrist of a user, a processing unit connected to the band and a drug delivery unit connected to the band. The processing unit comprises at least one sensor, wherein the at least one sensor is configured to determine one or more body parameters of a user; a reservoir containing a drug; a processor communicably coupled to the at least one sensor, wherein the processor is configured to receive one or more signals indicative of the one or more body parameters from the at least one sensor and determine a quantity of the drug to be delivered from the reservoir based on one or more body parameters; a pump configured to regulate discharge of the drug from the reservoir based on the determined quantity of the drug; and a signal generator configured to generate electrical signals based on control instructions received from the processor. The drug delivery unit comprises a chamber configured to receive the determined quantity of the drug from the reservoir and a transducer connected to the chamber, wherein the transducer is configured to transdermally deliver the drug from the chamber to skin of the user based on an electrical signal received from the signal generator.

These and other advantages will be apparent from the present application of the embodiments described herein.

The preceding is a simplified summary to provide an understanding of some aspects of embodiments of the present invention. This summary is neither an extensive nor exhaustive overview of the present invention and its various embodiments. The summary presents selected concepts of the embodiments of the present invention in a simplified form as an introduction to the more detailed description presented below. As will be appreciated, other embodiments of the present invention are possible utilizing, alone or in combination, one or more of the features set forth above or described in detail below.

BRIEF DESCRIPTION OF THE DRAWINGS

The accompanying drawings, which are incorporated in and constitute a part of this specification, illustrate several embodiments of the disclosure and, together with the description, explain the principles of the disclosure, and wherein.

Figure 1:
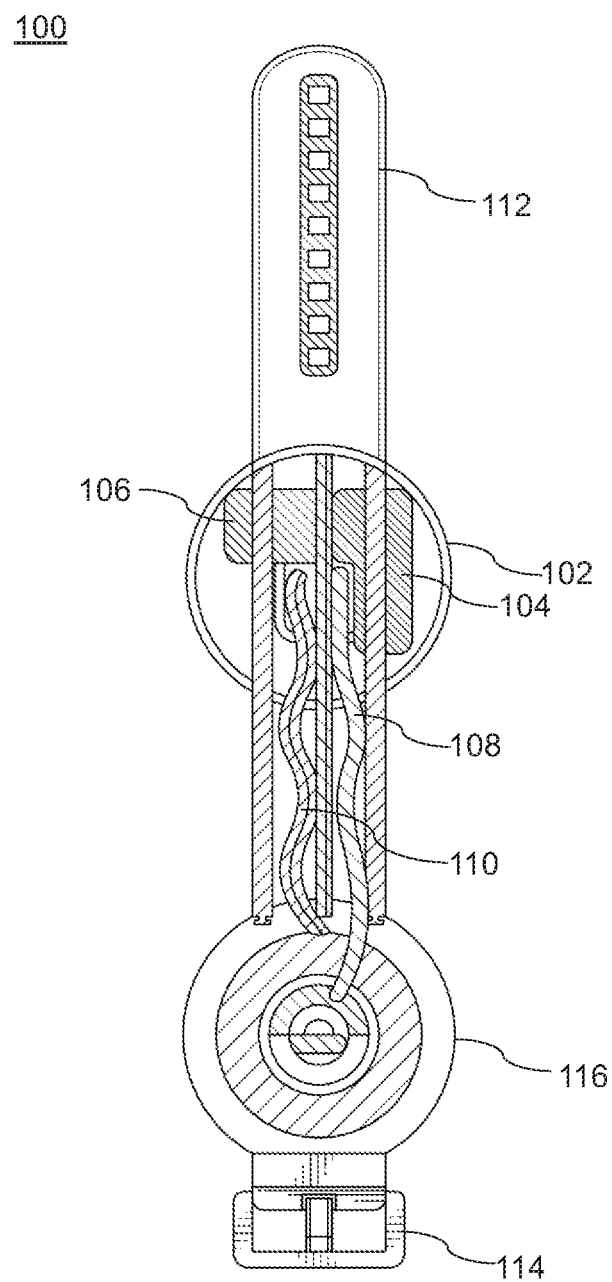
FIG. 1 illustrates a wearable device for drug delivery, in accordance with an embodiment of the present invention.

While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the form disclosed, but to the contrary, the present disclosure is to cover all modification, equivalents and alternatives falling within the spirit and scope of embodiments of the present disclosure as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

As used throughout this application, the word "may" is used in a permissive sense (i.e., meaning having the potential to), rather than the mandatory sense (i.e., meaning must). Similarly, the words "include", "including", and "includes" mean including but not limited to.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The present invention is directed to a device for drug delivery. The device includes a processing unit that may be detachably attached to skin of a user. The processing unit includes one or more sensors, a processor, a signal generator and a drug reservoir. A pump is attached to the reservoir. The sensors in the processing unit determine one or more body parameters of the user. Signals indicative of the body parameters are transmitted to the processor. Based on the received signals, the processor determines the quantity of drug to be discharged from the reservoir. The drug is transported from the reservoir to a drug delivery unit through a drug tube. The drug delivery unit may be detachably attached to the skin of the user, and further includes a chamber that receives the drug from the reservoir, a transducer connected to the chamber and a transdermal patch disposed below the chamber. The transducer is communicably coupled to the signal generator through a communication interface (e.g., electrical wires or a wireless interface).

The chamber of the drug delivery unit receives the drug from the reservoir through drug tubes. In an embodiment, the transducer surrounds the chamber within the drug delivery unit. The transducer includes multiple piezoelectric plates. Ultrasonic vibrations from the piezoelectric plates facilitate in widening the pores on the skin and/or the transdermal patch. The drug is delivered to the skin from the transdermal patch. The drug enters the bloodstream through pores such as hair follicles, sweat pores and sebaceous pores on the skin of the user.

FIG. 1 illustrates a wearable device 100 for drug delivery. The device 100 includes a processing unit 102. The processing unit includes one or more sensors (not shown in FIG. 1A), a processor (not shown), a signal generator, a reservoir 106 to contain a drug and a pump 104. The processing unit 102 is disposed on a band 112. The band 112 may be worn on a wrist or any applicable part of the user by securing the band 112 to a buckle 114. A drug delivery unit 116 is also disposed on the band 112. The processing unit 102 and the drug delivery unit 116 are connected by a drug tube 108 and one or more wires 110. The drug tube 108 and the wires 110 are disposed within the band 112.

In an example, the drug in the reservoir 106 may be an antibiotic. The sensors may determine the temperature of the user to whom the device 100 is detachably attached. Accordingly, the antibiotic may be transported to the drug delivery unit through the drug tube 108. In another example, the drug in the reservoir 106 may be insulin. The processing unit sensors may determine the blood glucose levels of the user wherein the insulin may be transported to the drug delivery unit through the drug tube 108 and dispensed accordingly.

As illustrated, the wearable device 100 is shown as a wrist watch with a band. The wearable device 100 may be connected to any kind of attachment structure, such as, but not limited to, a strap, clasp, or any other attachment structure without departing from the scope of the present invention.

Figure 2A:
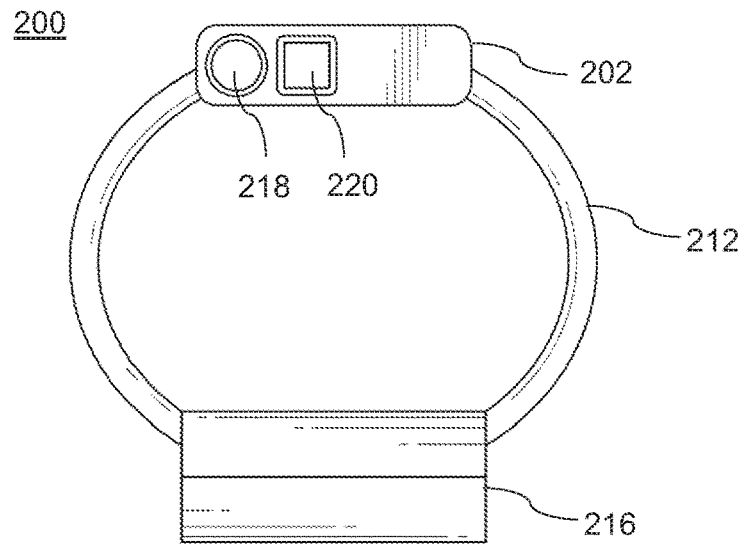
FIG. 2A illustrates a side view of a wearable device for drug delivery, in accordance with an embodiment of the present invention.

FIG. 2A illustrates a device 200 with a band 212 being secured to a buckle (not shown in FIG. 2A). The device 200 is similar to the device 100 (shown in FIG. 1) except that the drug delivery unit 216 has a different shape. Further, the device 200 may be worn on the wrist of a user. The device 200 includes a processing unit 202 and a drug delivery unit 216, both of which are attached to the band 212. The processing unit 202 may be disposed on a dorsal side of the wrist. The processing unit 202 includes ports 218 and 220 on the side. The port 218 may be an input/output port that is used to interface the device 200 with an external computer or external memory to provide data transfer functionalities. The port 220 may be a charging port. The ports 218 and 220 may include interfaces, such as, but not limiting to, Universal Serial Bus (USB), USB-C, a Lightening connector, optical connector, micro-USB and the like. The charging port 220 is used to connect the device 200 to an external power source in order to charge the battery disposed within the processing unit 202. In some embodiments, the device 200 may include output ports of various sizes and type. The output port may be, but not limited to a 3.5 millimeter audio jack, a video serial port, an audio/visual (AV) port, a VGA (Video Graphics Array), a HDMI (High Definition Multimedia Interface) port, a DVI (Digital Visual Interface) port, and a FireWire (IEEE 1394) port.

The processing unit 202 further includes multiple sensors (not shown in FIG. 2A), a processor (not shown in FIG. 2A), a signal generator (not shown in FIG. 2A), a reservoir (not shown in FIG. 2A) containing a drug and a pump (not shown in FIG. 2A) connected to the reservoir. The pump is also communicably coupled to the processor. Based on body parameters determined by the multiple sensors, the processor determines a quantity of the drug to be discharged from the reservoir. Accordingly, the determined quantity of the drug is transported to the drug delivery unit 216 through a drug tube. The pump regulates the amount of drug to be transported to the drug delivery unit 216. The drug tube is disposed within the band 212. The drug delivery unit 216 delivers the drug to the skin of the user.

Figure 2B:
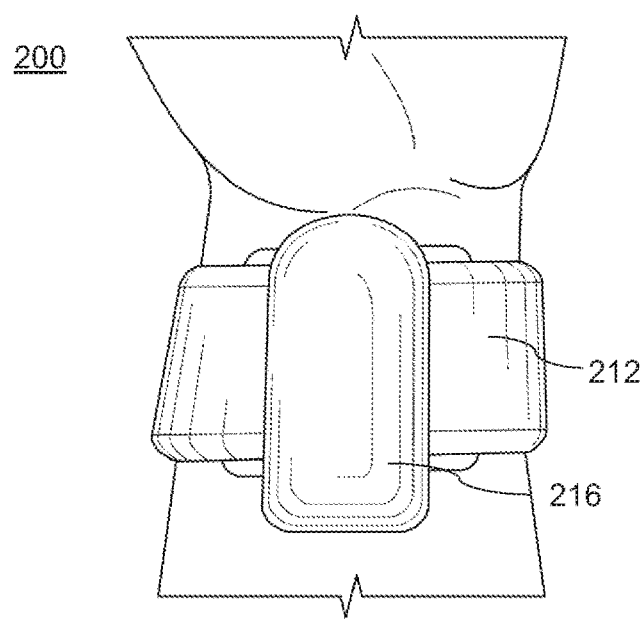
FIG. 2B illustrates the wearable device of FIG. 2A worn on a wrist.

FIG. 2B illustrates the device 200 being worn on a wrist of the user. As shown, the drug delivery unit 216 is placed on a ventral side of the wrist. The drug delivery unit 216 includes a transdermal patch (not shown) that is adhesively coupled to the skin of the user.

Figure 2C:
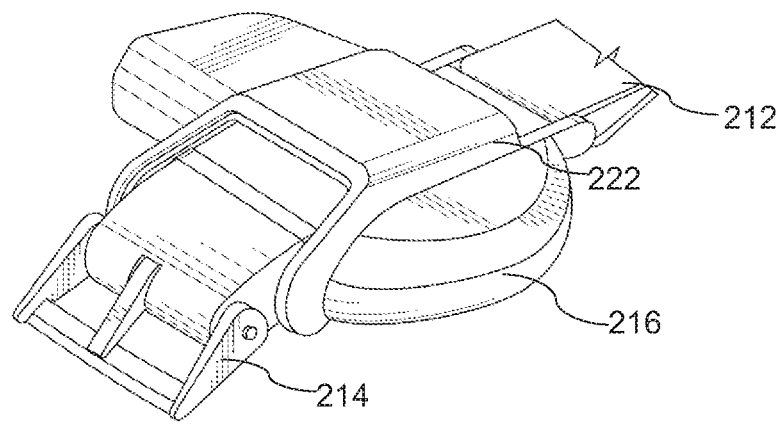
FIG. 2C illustrates a perspective view of the wearable device of FIG. 2A.

FIG. 2C illustrates a perspective view of the drug delivery unit 216 attached to the band 212. As shown in FIGS. 2A and 2B, the drug delivery unit 216 is placed on the ventral side of the wrist. The band 212 is worn on the wrist by securing the band 212 to the buckle 214. The band 212 is looped over the drug delivery unit 216 by sliding the band 212 through a holder 222. The holder 222 is attached to the band 212 and the drug delivery unit 216.

The drug delivery unit 216 includes a chamber (not shown) that receives the drug through one or more drug tubes disposed within the band 212. The drug tubes fluidically communicate the chamber of the drug delivery unit 216 with the reservoir of the processing unit 202. Further, the drug delivery unit 216 includes a transducer (not shown) that surrounds the chamber. The transducer has multiple piezoelectric plates. Each piezoelectric plate includes one or more piezoelectric crystals. The processor in the processing unit 202 is communicably coupled to the transducer through wires that are disposed within the band 212.

Figure 2D:
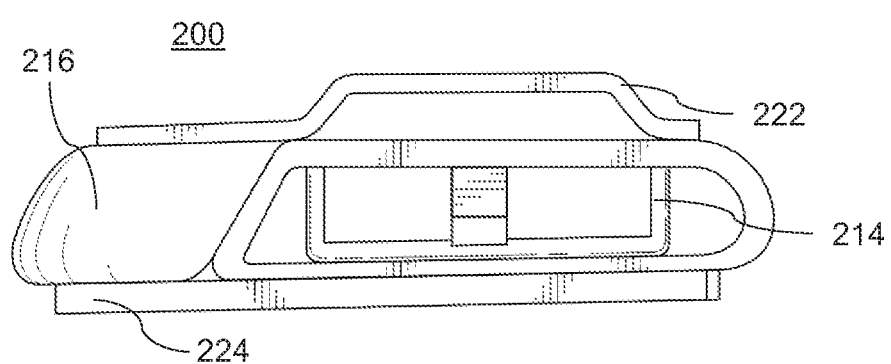
FIG. 2D illustrates a front view of the wearable device of FIG. 2A.

FIG. 2D illustrates a front view of the device 200. The device 200 includes a transdermal patch 224 attached to the drug delivery unit 216 on the side where the device 200 is in contact with skin. The transdermal patch 224 may be adhesively coupled to the skin. The transdermal patch 224 encapsulates drugs received from the chamber in the drug delivery unit 216. The transdermal patch 224 provides a controlled release of the drug into the user through the skin. The transdermal patch 224 may include one or more layers of a porous membrane that allows the drug to pass from the drug delivery unit 216 to the skin. A coupling medium may also be applied to each porous layer. The coupling medium may also be applied to the outermost porous layer of the transdermal patch 224 that faces the skin. In some embodiments, the coupling medium may be a composition of propylene glycol and water.

In some embodiments, the transdermal patch 224 may have enhanced permeation or increased porosity based on ultrasonic vibrations generated by the transducer in the drug delivery unit 216. The ultrasonic vibrations are generated by converting electrical signals transmitted by the signal generator. In some embodiments, the processor controls a power circuit in the processing unit 202 to send electrical signals to the transducer. The power circuit may be powered by the battery. In some embodiments, the electrical signals are transmitted to the transducer after delivery of the drug from the reservoir to the chamber via the drug tubes disposed in the band 212. The electrical signals may be alternating signals that are transmitted to the piezoelectric plates at the resonance frequencies of the piezoelectric crystals contained within the piezoelectric plates.

Ultrasonic vibrations alternately compress and stretch a molecular spacing in the coupling medium. Tiny bubbles are generated when ultrasound waves travel through the coupling medium. These bubbles move chaotically and implode when they reach a certain size. Surrounding fluid flows into the empty space, generating high-speed micro jets of fluid that create microscopic abrasions on the skin. The microscopic abrasions result in temporary cavitation in the skin, thereby providing micro channels through which a drug may be delivered.

In some embodiments, the coupling medium may be applied to the transducer. The transducer may be in contact with the skin with a layer or multiple layers of the coupling medium separating the skin and the transducer.

In some embodiments, the transdermal patch 224 may also include a permeation enhancer that increases the delivery of the drug to the skin. A permeation enhancer may increase the rate at which the drug is delivered through the skin. Examples of a permeation enhancer may be, but not limited to, dimethyl sulfoxide, dimethylformamide, dimethylacetamide and the like.

Figure 3A:
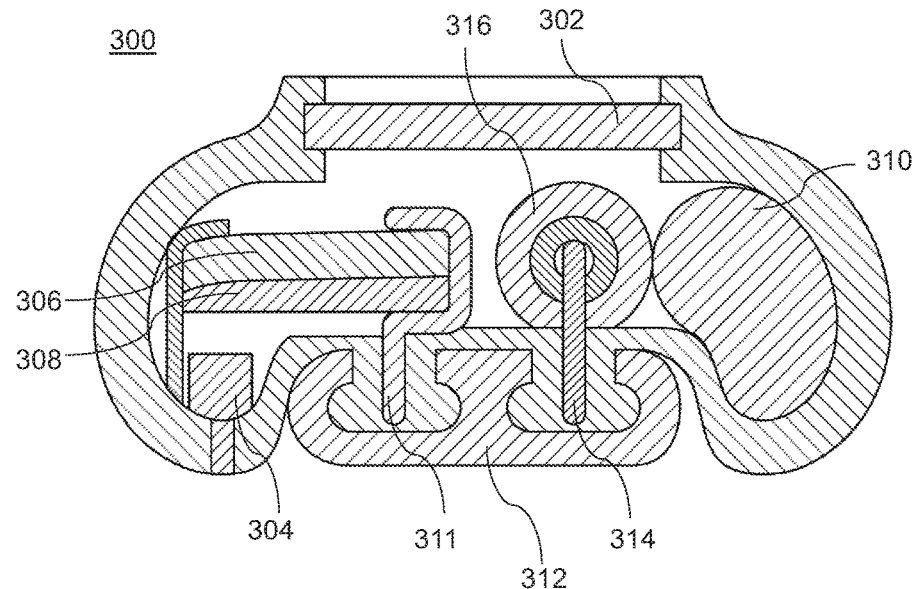
FIG. 3A illustrates a sectional view of a processing unit that is part of a wearable device, in accordance with an embodiment of the present invention.
Figure 3B:
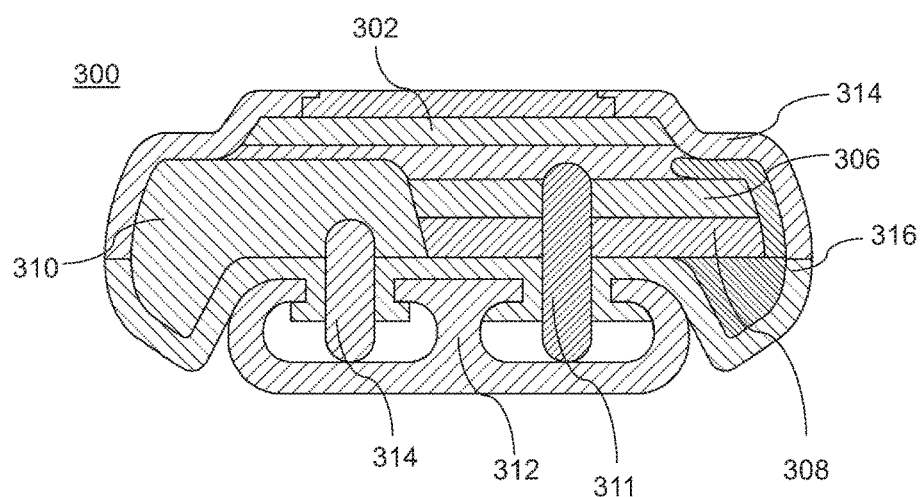
FIG. 3B illustrates another sectional view of the processing unit of FIG. 3A.

FIGS. 3A and 3B illustrate sectional views of a processing unit 300 disposed on a band 312. The processing unit 300 is similar to the processing unit 202 (shown in FIG. 2). The processing unit 300 may be part of the device 200 which includes a drug delivery unit disposed on the band 312 in a similar manner as shown in FIGS. 2A, 2B, 2C and 2D. The processing unit 300 and the drug delivery unit are connected through a wire 311 and a drug tube 314.

The processing unit 300 encloses various components. As shown in FIGS. 3A and 3B, the processing unit 300 includes one or more sensors 304, a processor (not shown in FIGS. 3A and 3B) disposed on a printed circuit board 306 (PCB 306), a signal generator (not shown in FIGS. 3A and 3B), a battery 308, a reservoir containing a drug 310 and a pump 316. In an embodiment, the signal generator may also be disposed on the PCB 306. The processing unit 300 is disposed on the band 312. The battery 308 is communicably coupled to the PCB 306. Further the processing unit 300 includes a screen 302 communicably coupled to the processor.

The processor may be, but not restricted to, a Central Processing Unit (CPU), a microprocessor, or a microcontroller. The signal generator may include a power circuit that generates electrical signals to be transmitted to the drug delivery unit. The PCB 306 may also include a memory, input/output ports, a clock, and the like.

The pump 316 is attached to the reservoir 310. The pump 316 may also be communicably coupled to the PCB 306. The sensors 304 in the processing unit 300 determine one or more body parameters of the user. Signals indicative of the body parameters are transmitted to the processor disposed on the PCB 306. Based on the received signals, the processor determines a quantity of the drug to be discharged from the reservoir 310. The drug is transported from the reservoir 310 to the drug delivery unit through the drug tube 314. The pump 316 regulates the amount of drug to be transported to the drug delivery unit.

In some embodiments, the pump 316 may be a micropump that includes a membrane or a diaphragm and one or more check valves integrated on a Micro ElectroMechanical (MEMS) chip. The MEMS chip is a stack of one or more layers bonded together. The layers may include a silicon on insulator plate with micromachined pump structures and cover plates. The MEMS chip may be assembled with an actuator that moves the membrane in a reciprocating movement to compress the drug in the reservoir 310. The check valves are used to prevent backflow of the drug into the reservoir 310. The actuator may be controlled by a piezoelectric mechanism. The signal generator may transmit electrical signals to the piezoelectric mechanism, thereby converting electrical energy to mechanical movement or actuation. Based on the quantity of the drug determined by the processor, the processor controls the signal generator to provide electrical signals of a specific frequency, such that the pump 316 is actuated to allow the determined quantity of the drug to be discharged from the reservoir 310.

In some embodiments, the sensors 304 are a bio-sensor that determines one or body parameters based on sweat of the user that is in contact with the sensors 304. The processor is configured to generate one or more indicia based on the body parameters. The processor further generates a user interface for displaying the indicia. The screen 302 displays the indicia. In another embodiment of the present invention, the indicia generated may be transferred, displayed and saved to a separate mobile electronic device, including but not limited to a mobile phone, laptop, home computer, and the like.

In an example, the processing unit 300 may be part of a drug delivery device that is used for insulin delivery to a user. Accordingly, the reservoir 310 is filled with insulin. The sensors 304 may detect an amount of glucose prevalent in sweat. Accordingly, a signal indicative of the amount of glucose is transmitted to the processor on the PCB 306. The processor determines a quantity of the insulin needed to be delivered to the user. Based on the determined quantity, the processor controls the signal generator, such that the signal generator transmits an alternating electrical signal of a specific frequency and amplitude to the pump 316. Based on the electrical signal, the pump 316 is actuated to allow a discharge of the insulin from the reservoir 310 to the drug delivery unit. The amount of insulin discharged is equivalent to the quantity of the drug determined by the processor. Accordingly, the pump 316 regulates the amount of insulin to be transported. The determined quantity of the insulin is transported from the reservoir 310 to the drug delivery unit via the drug tube 314.

Figure 4A:
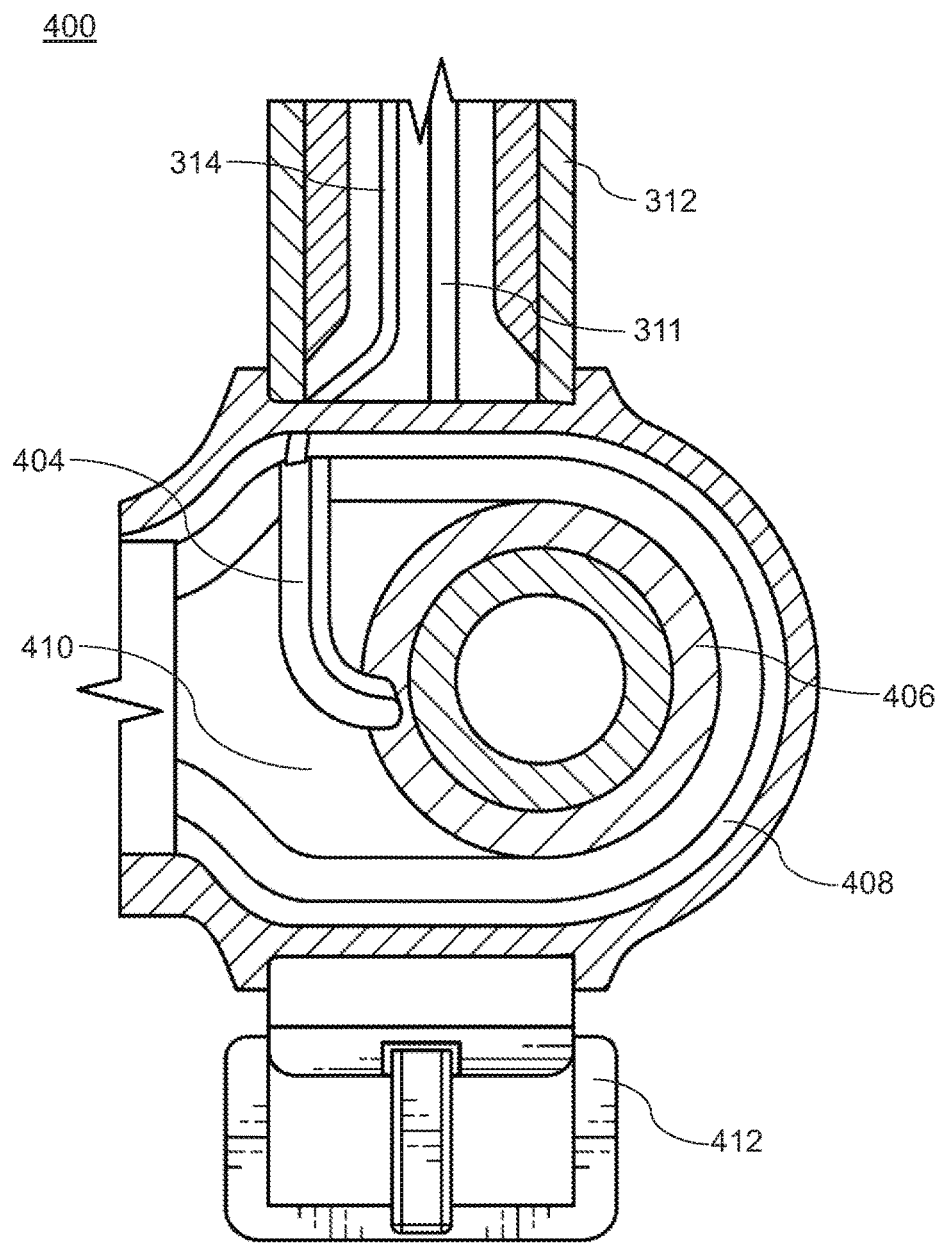
FIG. 4A illustrates a sectional view of a drug delivery unit that is part of a wearable device, in accordance with an embodiment of the present invention.

FIG. 4A illustrates a sectional view of a drug delivery unit 400 connected to the processing unit 300 (shown in FIGS. 3A and 3B). The drug delivery unit 400 and the processing unit 300 are disposed on the band 312. The drug delivery unit 400 includes a transducer 406 enclosed in a silicon casing 408. The silicon casing 408 seals the transducer 406 and a chamber 410 placed adjacent to the transducer 406. The chamber 410 receives a quantity of the drug from the processing unit 300 through the drug tube 314. The drug tube 314 may be partially enclosed within a casing 404. The quantity of the drug is determined by the processor disposed on the PCB 306 (shown in FIG. 3A). The drug tube 314 is disposed within the band 312. A buckle 412 is attached to the drug delivery unit. The buckle 412 is used to secure the band 312 in a loop such that the processing unit 300 and the drug delivery unit 400 may be worn on a wrist. In some embodiments, the processing unit 300, the drug delivery unit and the band may be worn around any other body part, for example, the waist, in a looping manner.

The transducer 406 includes multiple piezoelectric plates. In some embodiments, the transducer 406 may be a cymbal transducer. A cymbal transducer is a flextensional transducer capable of producing ultrasonic waves or vibrations. The transducer 406 may have a compact, lightweight structure with an adjustable resonance frequency. The transducer 406 may include multiple piezoelectric plates sandwiched between cymbal-shaped metal end-caps bonded directly to a surface of the piezoelectric plate. The transducer 406 is surrounded by the silicon casing 408. In some embodiments, the transducer 406 includes an assembly of circular piezoelectric plates. In other embodiments, the transducer 406 may include piezoelectric plates having polygonal shapes.

Figure 4B:
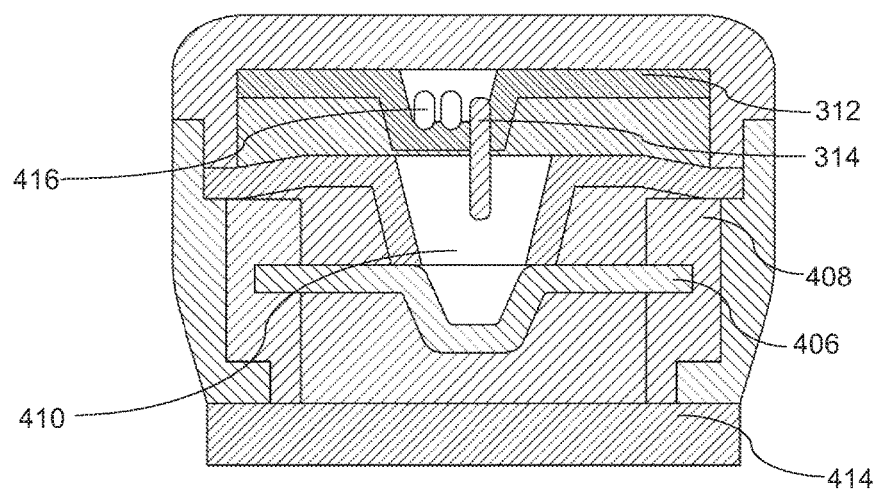
FIG. 4B illustrates another sectional view of the drug delivery unit of FIG. 4A.
Figure 4C:
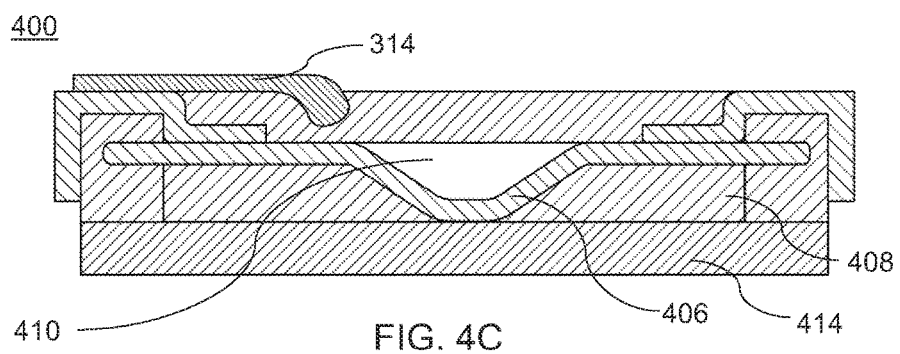
FIG. 4C illustrates yet another sectional view of the drug delivery unit of FIG. 4A.

FIGS. 4B and 4C illustrate sectional views of the drug delivery unit 400. A drug is transported from the processing unit 300 to the chamber 410 through the drug tube 314 disposed within the band 312. The drug is delivered to the skin of the user through a transdermal patch 414 disposed below the chamber 410. The transdermal patch 414 may be adhesively coupled to the skin. The transdermal patch 414 encapsulates drugs received from the chamber 410. The transdermal patch 414 provides a controlled release of the drug into the user through the skin. The transdermal patch 414 may include multiple layers of a porous membrane that allows the drug to pass to the skin. A coupling medium may be applied to each porous layer. The coupling medium may also be applied to the outermost porous layer of the transdermal patch 414 that faces the skin. In some embodiments, the coupling medium may be a composition of propylene glycol and water.

The transducer 406 receives alternating current signals from the signal generator in the processing unit 300 through wires 416. In an embodiment, the wires 416 may be connected to the wire 311 (shown in FIG. 3A). The wires 416 may ensure reliable communication between the transducer 406 and the signal generator. The wires 416 are disposed within the band 312. The piezoelectric crystal in the transducer 406 undergoes rhythmic deformation due to the alternating current signals, thereby generating ultrasonic vibrations. In some embodiments, the piezoelectric crystals change size and shape when a voltage is applied. FIG. 4C illustrates a change in shape in the piezoelectric plates of the transducer 406. The intensity of ultrasonic vibrations may be dependent on the alternating current signals and a gap between the transducer 406 and the transdermal patch 414.

Ultrasonic vibrations from the transducer 406 alternately compress and stretch a molecular spacing in the coupling medium. Tiny bubbles are generated when ultrasound waves travel through the coupling medium. These bubbles move chaotically and implode when they reach a certain size. Surrounding fluid flows into the empty space, generating high-speed micro jets of fluid that create microscopic abrasions on the skin. The microscopic abrasions result in temporary cavitation in the skin, thereby providing micro channels through which a drug may be delivered.

In some embodiments, microscopic abrasions on the skin are accomplished by applying relatively low frequency (for example 5 KHz-1 MHz) ultrasonic stimulation pulses through the skin for a predetermined period of time. Thereafter, higher variable frequency (for example, 50 MHz-300 MHz) pulses are applied to the skin. Accordingly, electrical signals transmitted to the transducer 406 are varied by the signal generator. Applying variable frequencies facilitates drug delivery from the chamber 410 to the transdermal patch 414 and drug delivery from the transdermal patch 414 to the skin.

Figure 5:
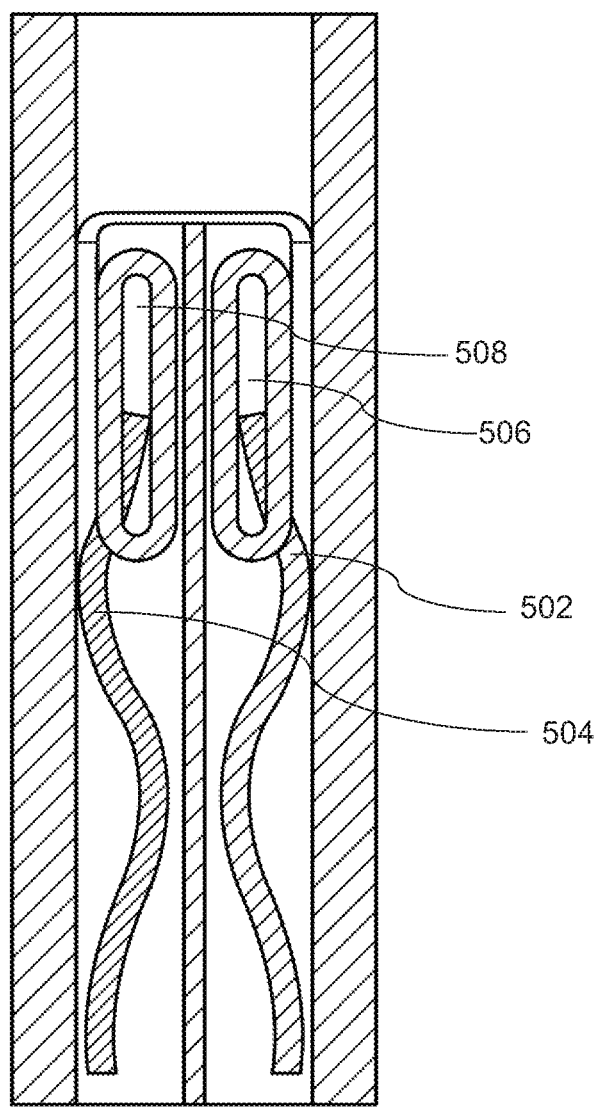
FIG. 5 illustrates a sectional view of a band that is part of a wearable device, in accordance with an embodiment of the present invention.

FIG. 5 illustrates a sectional view of an adjustable band 500. The band 500 may be, but not limited to, a wrist band or a strap. In some embodiments, the band 500 may be worn over a wrist. The band 500 may include conductive and non-conductive elements. In some embodiments, the band 500 may include multiple modular band links. The band 500 may further include one or more electronic components that are electrically, structurally and communicably connected to the processing unit 300 (shown in FIG. 3A) and the drug delivery unit 400 (shown in FIG. 4A). One or more wires 502 and a drug tube 504 are disposed within the band 500. The wires 502 connect the transducer 406 to a signal generator in the processing unit 300 and the drug tube 504 connects the pump 316 to the chamber 410. The wires 502 and the drug tube 504 may be movable at openings 506 and 508, respectively. In some embodiments, the positions of the wires 502 and the drug tube 504 may be adjusted through the openings 506 and 508, respectively.

Figure 6A:
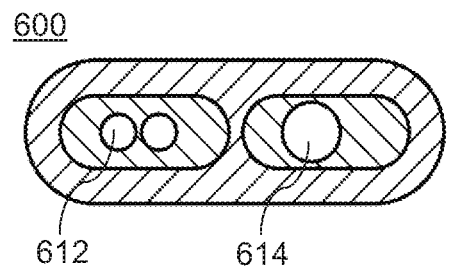
FIG. 6A illustrates a sectional view of a modular link that is part of a band, in accordance with an embodiment of the present invention.
Figure 6B:
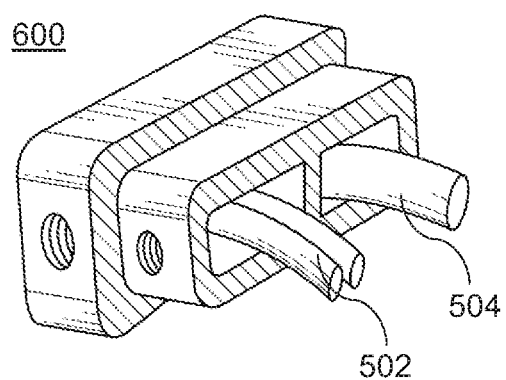
FIG. 6B illustrates a sectional perspective view of the modular link of FIG. 6A.

FIG. 6A illustrates a sectional view of a modular link 600 with ports 612 for the wires 502 (shown in FIG. 5) and a port 614 for the drug tube 504 (shown in FIG. 5). FIG. 6B illustrates a sectional view of the modular link 600 with the wires 502 and the drug tube 504 passing through the respective ports.

Figure 7:
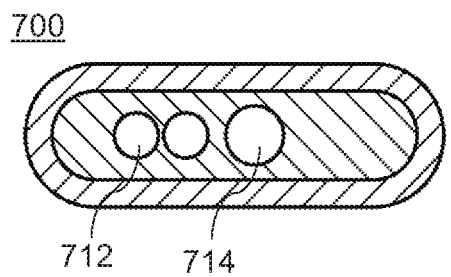
FIG. 7 illustrates a sectional view of a modular link that is part of a band, in accordance with an embodiment of the present invention.

FIG. 7 illustrates a sectional view of a modular link 700 with a different configuration of ports shown in FIG. 6A. The modular link 700 includes ports 712 for the wires 502 (shown in FIG. 5) and a port 714 for the drug tube 504 (shown in FIG. 5). In some embodiments, the band 500 (shown in FIG. 5) may be made up of multiple modular links similar to the modular links 600 and/or 700.

Figure 8:
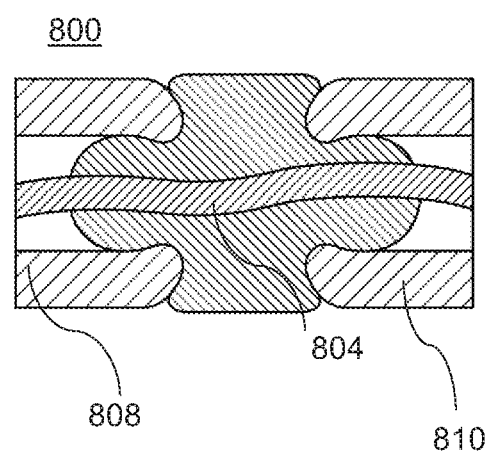
FIG. 8 illustrates a sectional view of two modular links in a band, in accordance with an embodiment of the present invention.

FIG. 8 illustrates a sectional view of a band 800 showing a modular link 808 linked to a modular link 810 with a drug tube 804 passing through each of the modular links 808 and 810.

Figure 9:
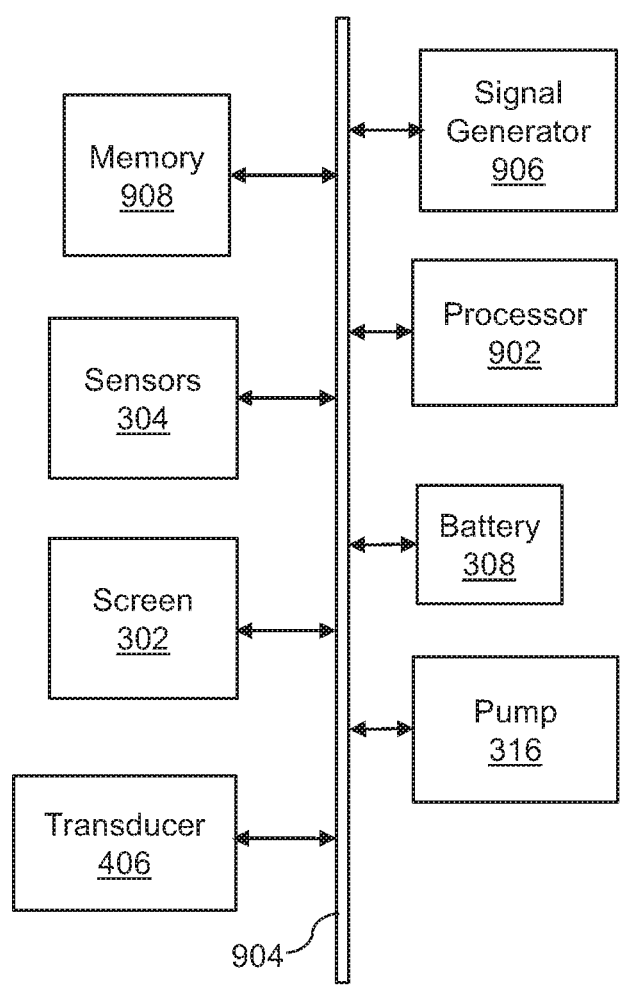
FIG. 9 illustrates a block diagram of a wearable device for drug delivery, in accordance with an embodiment of the present invention.

FIG. 9 illustrates a system 900, in accordance with an embodiment of the present invention. The system 900 may be part of any of the devices 100 (shown in FIG. 1) or 200 (shown in FIGS. 2A and 2B). The device 200 includes the processing unit 300 (shown in FIG. 3A) that is detachably attached to skin of a user. The processing unit 300 includes one or more sensors 304, a processor 902, a signal generator 906, a memory 908, the battery 308, the pump 316 and the reservoir 310 (shown in FIG. 3A). In an embodiment, the memory 908 may store instructions and/or data that are required for the operation of the processing unit 300. The pump 316 is attached to the reservoir 310. The sensors 304 in the processing unit 300 determine one or more body parameters of the user.

The device 200 includes a communication mechanism, such as an electrical bus 904 (hereinafter "the bus 904"). Signals indicative of the body parameters are transmitted to the processor 902 through the bus 904. The bus 904 is used to exchange information and/or signals between the internal components of the device 200. The bus 904 includes one or more parallel conductors of information so that information is transferred quickly among devices coupled to the bus 904. In some embodiments, the bus 904 is indicative of the wires 502 disposed within the band 500 (shown in FIG. 5). The processor 902, the signal generator 906, the sensors 304, the battery 308 and the transducer 406 (shown in FIG. 4A) are communicably coupled to the bus 904. Based on the received signals, the processor 902 determines the quantity of the drug to be discharged from the reservoir 310. Accordingly, the processor 902 may regulate the pump 316 to allow discharge of the determined quantity of the drug from the reservoir 310. In an embodiment, the processor 902 transmits control instructions to the pump 316 via the bus 904 to regulate operation of the pump 316. The drug is transported from the reservoir 310 to the chamber 410 (shown in FIG. 4A) through the drug tube 504.

In an embodiment, the processor 902 transmits control instructions, via the bus 904, to the signal generator 906 to regulate operation of the signal generator 906. The signal generator 906 generates electrical signals based on the control instructions received from the processor 902 via the bus 904. The electrical signals from the signal generator 906 are transmitted to the transducer 406 through the bus 904. The signal generator 906 may include circuitry pertaining to signal amplification, clocks, electronic oscillators, analog-to-digital converters, digital-to-analog converters, signal multiplexing and the like. The signal generator 906 further includes modulation circuits that facilitate in providing amplitude modulation, frequency modulation or phase modulation.

The transducer 406 generates ultrasonic vibrations based on the electrical signals. Ultrasonic vibrations from the piezoelectric plates facilitate in widening the pores on the skin and the transdermal patch 414 (shown in FIGS. 4A and 4B). The drug is delivered to the skin from the transdermal patch to the skin of the user. The drug enters the bloodstream through pores, such as hair follicles, sweat pores and sebaceous pores on the skin of the user.

In some embodiments, the transducer 406 may be made of porous ceramic piezoelectric plates. The piezoelectric material can be piezo-ceramic polymer composites, lead zirconate titanate, polyvinyl fluoride, thin-film zinc oxide, lead titanate, lead metaniobate, barium titanate or modified lead titanate. The transducer 406 may be located in the chamber 410. The drug passes through pores in the piezoelectric plates. Ultrasound waves are created when the signal generator 906 produces electrical energy that is converted to mechanical energy through the deformation of piezoelectric material in the transducer 406. The waves produced are transmitted by propagation through molecular oscillations in the drug.

The drug is delivered to the skin of the user through a transdermal patch 414 disposed below the chamber 410 and the transducer 406. The transdermal patch 414 is adhesively coupled to the skin. The transdermal patch 414 encapsulates drugs received from the chamber 410. The transdermal patch 414 provides a controlled release of the drug into the user through the skin. The transdermal patch 414 may include multiple layers of a porous membrane that allows the drug to pass to the skin. A coupling medium may be applied to each porous layer. The coupling medium may also be applied to the outermost porous layer of the transdermal patch 414 that faces the skin. Ultrasonic vibrations alternately compress and stretch a molecular spacing in the drug and the coupling medium. Tiny bubbles are generated when ultrasound waves travel through the drug and the coupling medium. These bubbles move chaotically and implode when they reach a certain size. Surrounding fluid flows into the empty space, generating high-speed micro jets of fluid that create microscopic abrasions on the skin. The microscopic abrasions result in temporary cavitation in the skin, thereby providing micro channels through which a drug may be delivered.

FIGS. 10A to 10D illustrate a user interface 1000 that displays indicia generated by the processor 902. The user interface 1000 may be displayed on the screen 302. In yet other embodiments of the present invention, the user interface 1000 and accompanying metrics may be transferred, displayed and saved to a separate mobile electronic device, including but not limited to a mobile phone, laptop, home computer, and the like. As illustrated, the user interface 1000 is shown to display indices pertaining to parameters for diabetes such as, but not limited to, insulin needed by the user, glucose level of the user, and the like. The wearable device 100 may connect to any kind of attachment structure such as, but not limited to, a strap, clasp, or any other attachment structure without departing from the scope of the present invention.

Figure 10A:
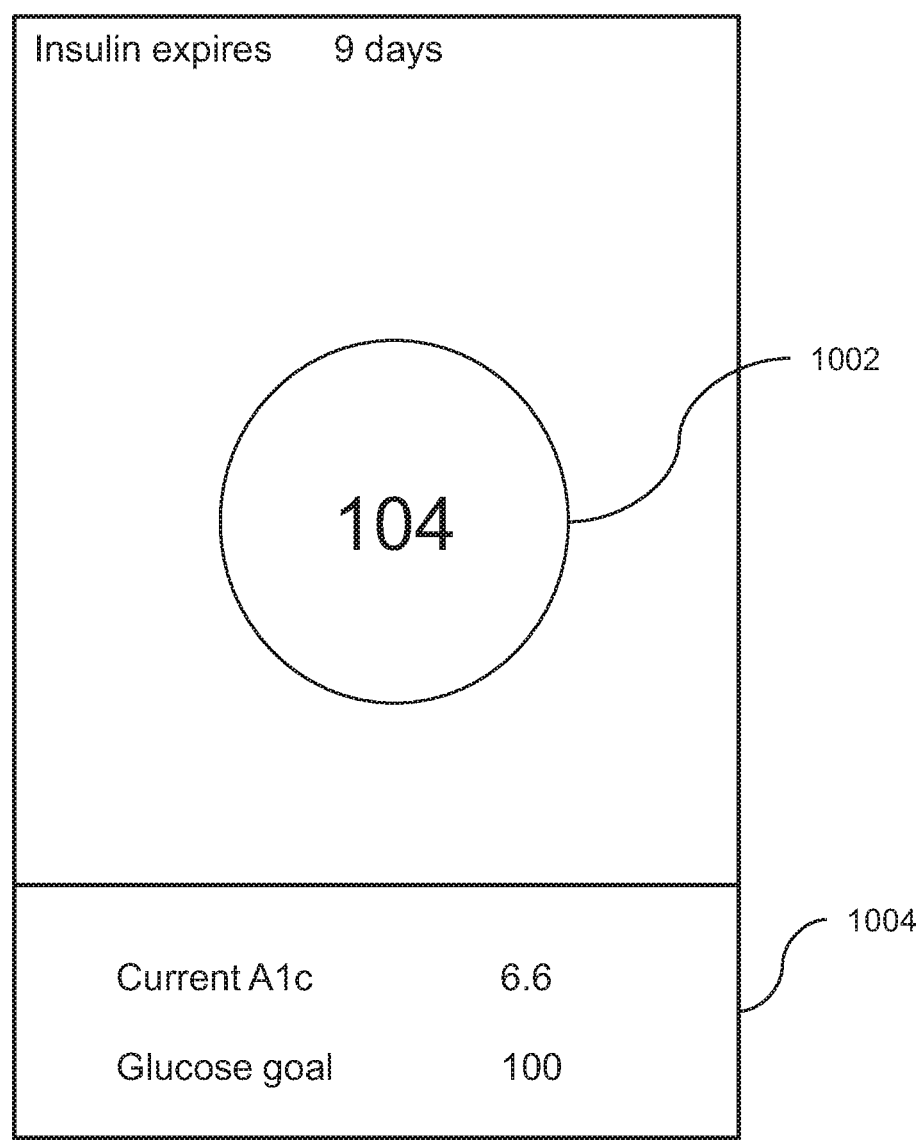
FIGS. 10A-10D illustrate screenshots of a user interface, in accordance with various embodiments of the present invention.

In FIG. 10A, the user interface 1000 shows a glucose level 1002 and metrics pertaining to A1c levels and future goals of the user. The glucose level may be determined by the sensors 304 (shown in FIG. 3A). In some embodiments, the user may also be directed to register an account with a health management system.

Figure 10B:
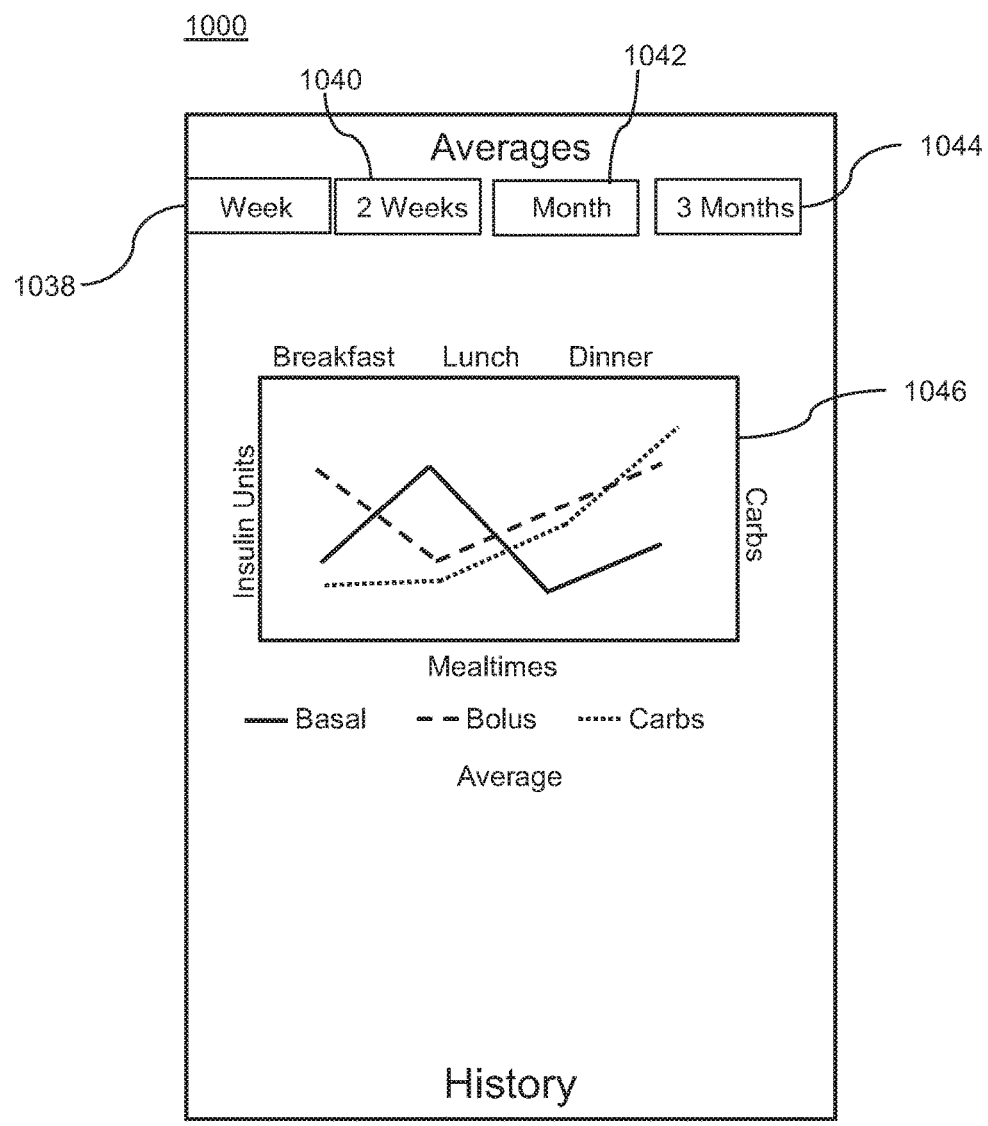

In FIG. 10B, a graph 1046, pertaining to average insulin dosages and average insulin to carbohydrate ratios, is represented on the user interface 1000. Graphical data with respect to a week, a fortnight, a month and three months may be displayed upon clicking the buttons 1038, 1040, 1042 and 1044, respectively.

Figure 10C:
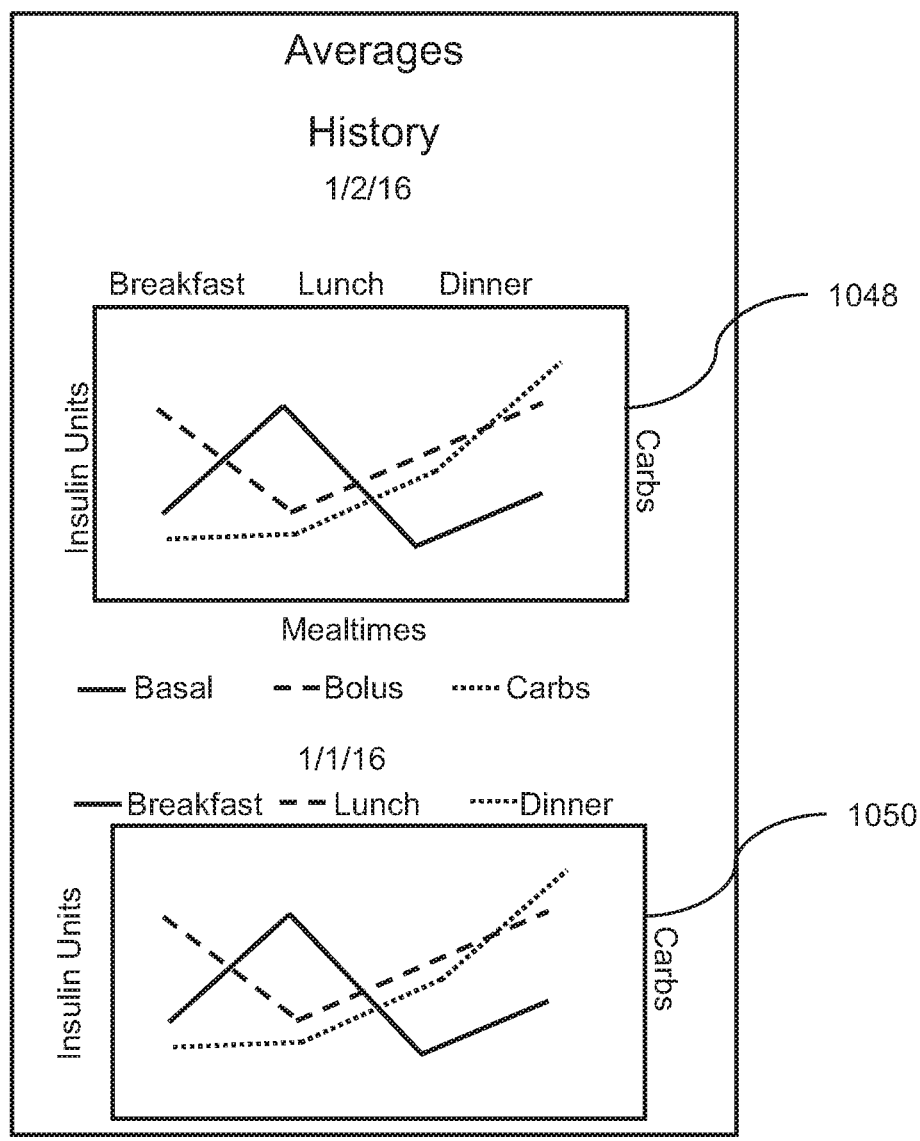
Figure 10D:
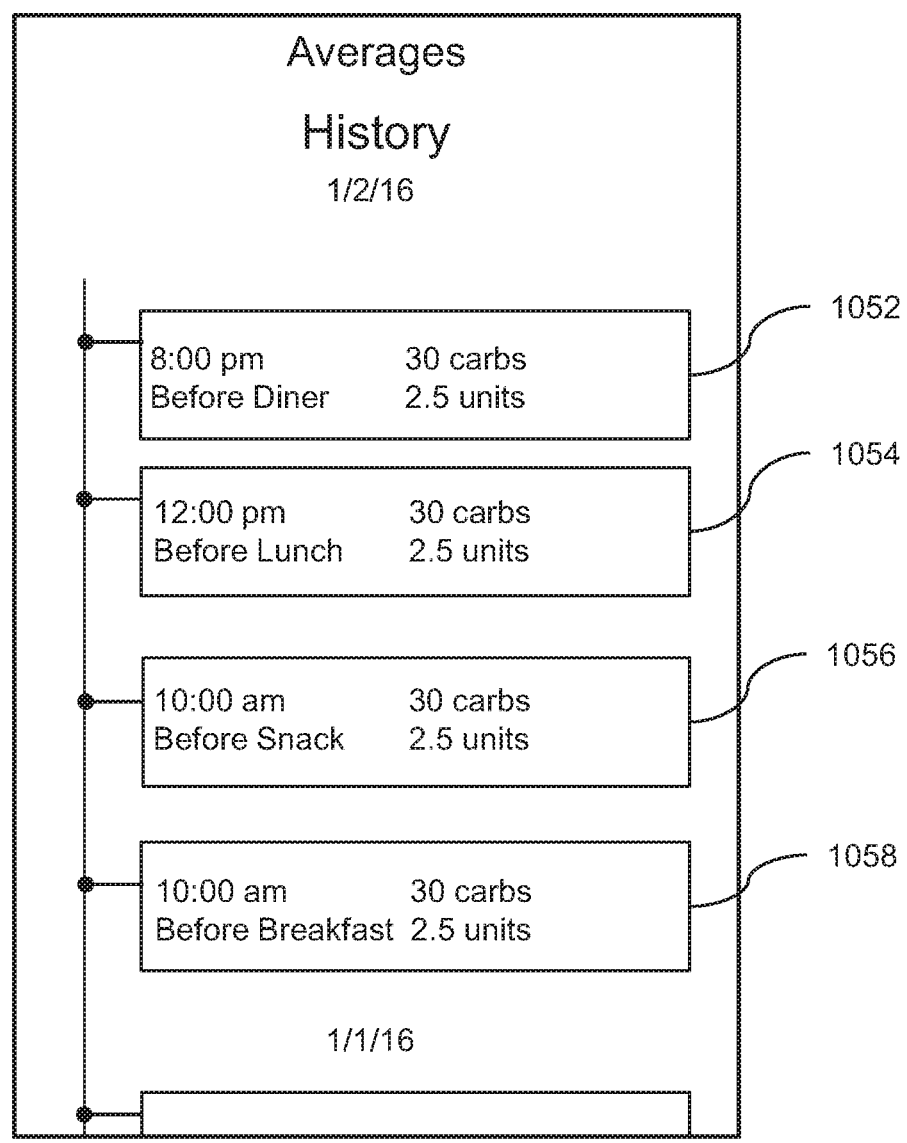
Figure 11A:
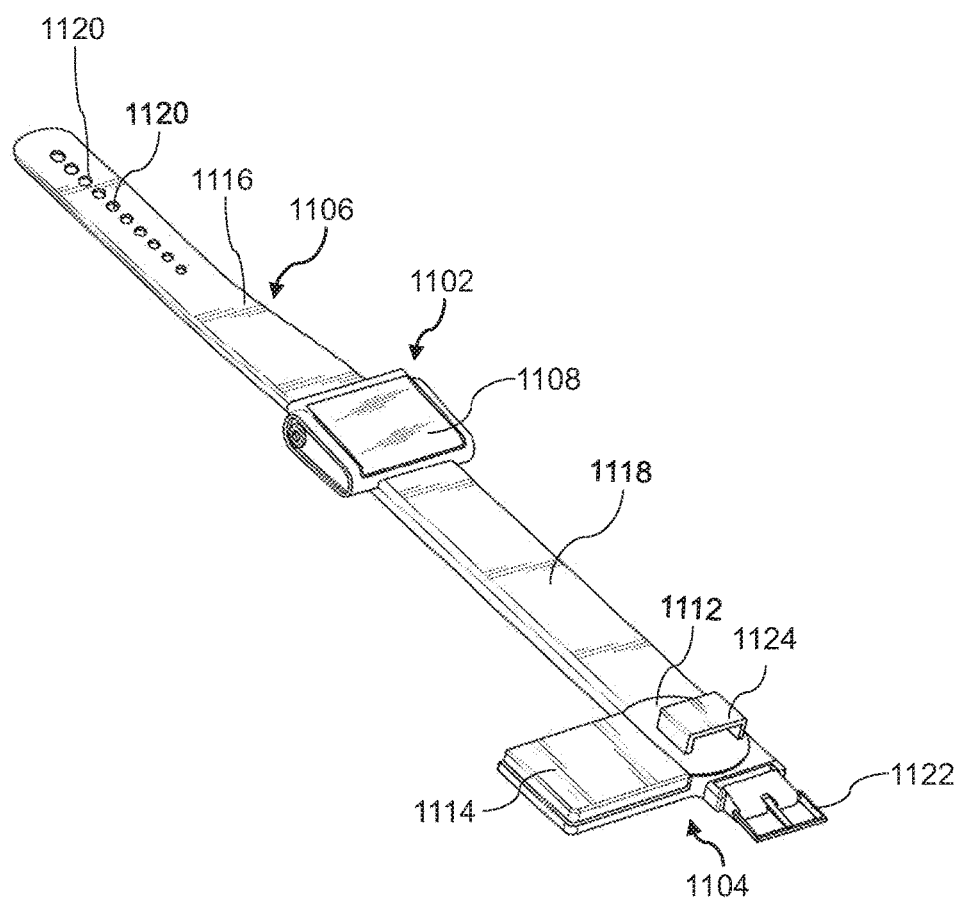
FIG. 11A is a front perspective view of a wearable device for drug delivery, in accordance with an embodiment of the present invention.
Figure 11B:
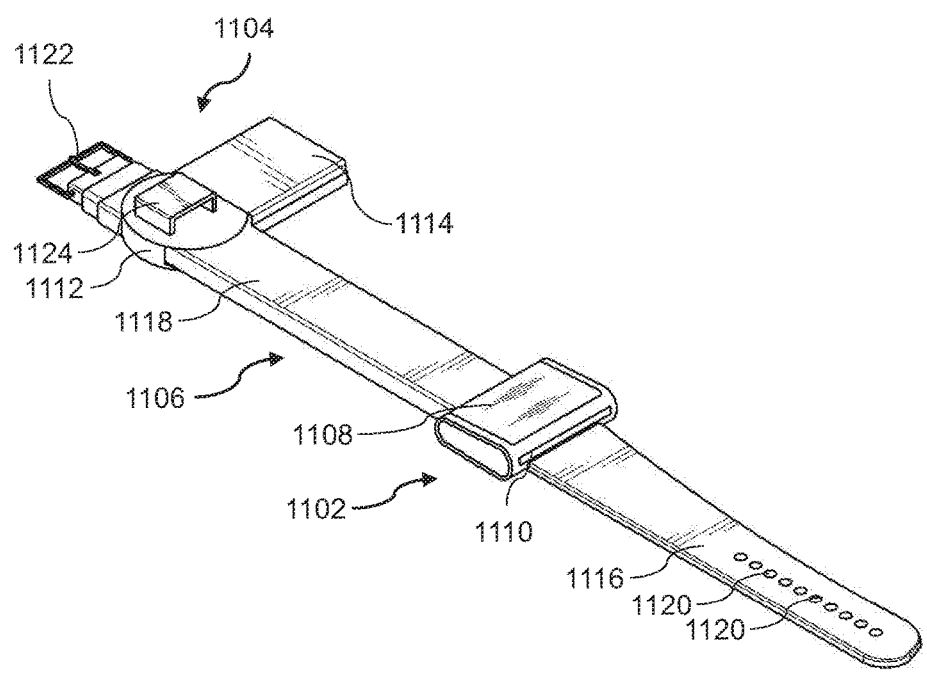
FIG. 11B is a rear perspective view of the wearable device of FIG. 11A.
Figure 11C:
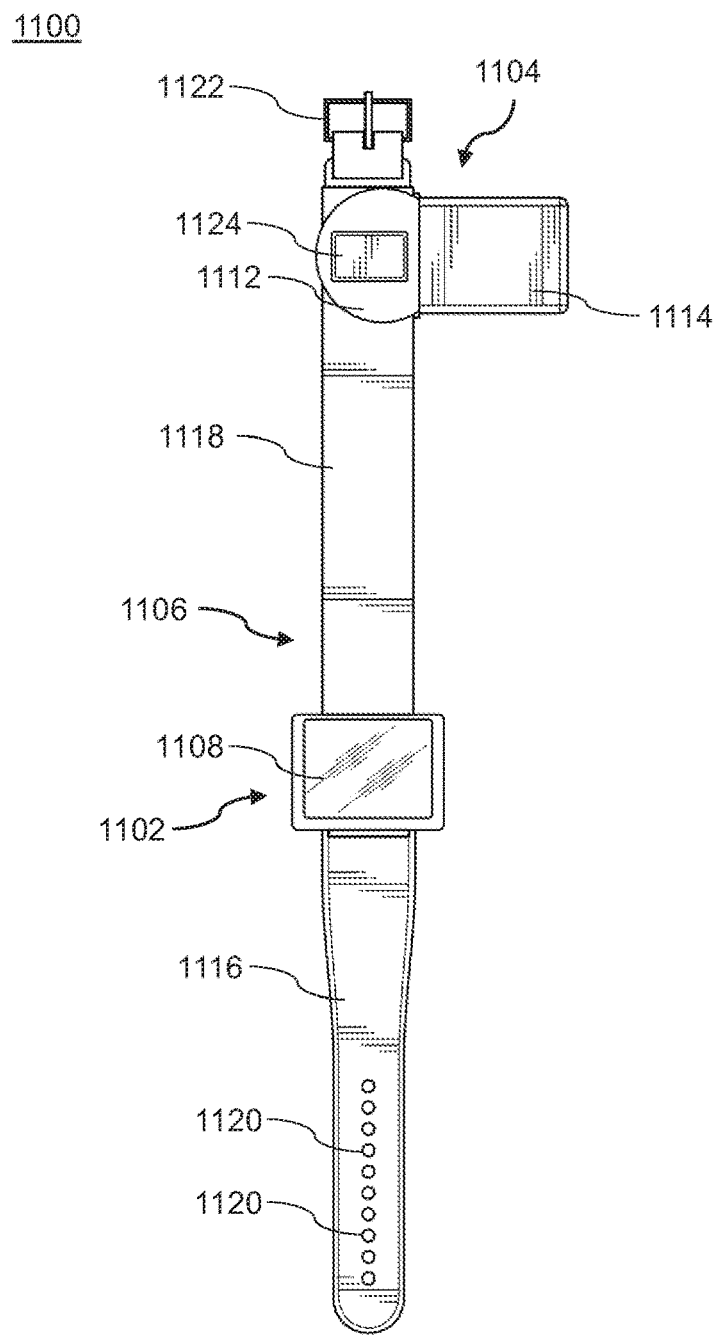
FIG. 11C is a top view of the wearable device of FIG. 11A.
Figure 11D:
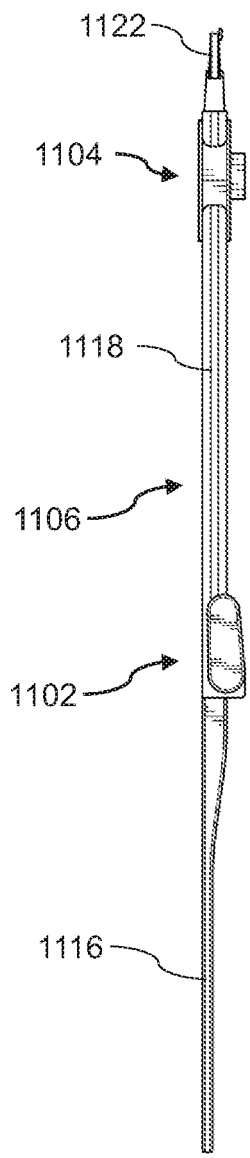
FIG. 11D is a left-side view of the wearable device of FIG. 11A.
Figure 11E:
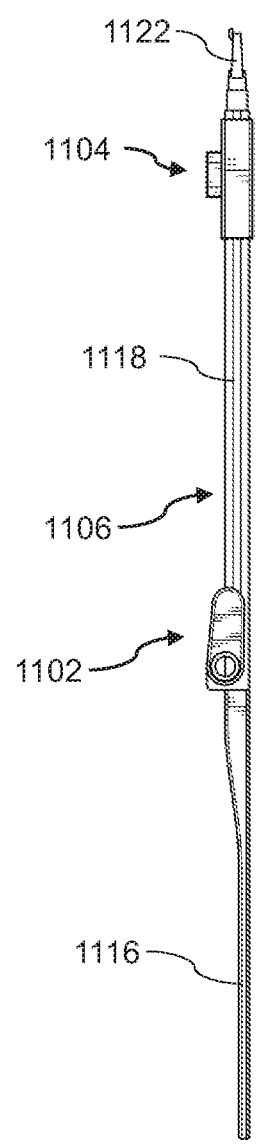
FIG. 11E is a right-side view of the wearable device of FIG. 11A.

In FIG. 10C, a graph 1048 displays insulin dosages and insulin to carbohydrate ratios for specific dates. The graph 1048 represents data tabulated on 2 Jan. 2016 and the graph 1050 represents data tabulated on 1 Jan. 2016. In FIG. 10D, a medical history of the user is displayed. Field boxes 1052, 1054, 1056 and 1058 display insulin to carbohydrate details at different times during a day.

FIGS. 11A to 11E illustrate various views of a wearable device 1100 for drug delivery, according to an embodiment of the present disclosure. The wearable device 1100 includes a processing unit 1102, a drug delivery unit 1104 and a band 1106 configured to be worn by a user. In the illustrated embodiment, the processing unit 1102 is shaped like a watch coupled with the band 1106. The processing unit 1102 and the drug delivery unit 1104 are disposed on the band 1106. The processing unit 1102 includes a first screen 1108 and a second screen 1110. The processing unit 1102 may be similar in functionality to the processing unit 202 (shown in FIG. 2A) or the processing unit 300 (shown in FIGS. 3A and 3B). Further, the drug delivery unit 1104 may be similar in functionality to the drug delivery unit 216 (shown in FIG. 2A) or the drug delivery unit 400 (shown in FIGS. 4A to 4C).

In an embodiment, the processing unit 1102 may include a sensor (not shown) that is configured to determine a body parameter of the user. The processing unit 1102 further includes a reservoir (not shown in FIGS. 11A to 11E) to store a drug (for example, insulin). The processing unit 1102 may also include a processor (not shown in FIGS. 11A to 11E) communicably coupled to the sensor. The processor receives a signal indicative of the body parameter from the sensor. The body parameter may be blood glucose level. The processor further determines a quantity of the drug to be delivered from the reservoir based on the body parameter. The processing unit also includes a signal generator (not shown in FIGS. 11A to 11E) that generates electrical signals based on control instructions received from the processor. The processor is further configured to generate indicia based on the body parameter and a user interface for displaying the indicia. The user interface may be displayed on the first screen 1108 and/or the second screen 1110. The processing unit 1102 may further include a pump (not shown in FIGS. 11A to 11E) to regulate discharge of the drug from the reservoir based on the determined quantity of the drug.

In an embodiment, the drug delivery unit 1104 includes a transducer (not shown in FIGS. 11A to 11E). The transducer receives the determined quantity of the drug from the reservoir of the processing unit 1102 via a drug tube (not shown in FIGS. 11A to 11E). Further, the transducer transdermally delivers the drug to skin of the user based on an electrical signal from the signal generator. In an embodiment, the transducer may be an ultrasonic transducer. The drug delivery unit 1104 may optionally include a transdermal patch (not shown in FIGS. 11A to 11E) adhesively coupled to the skin of the user. In another embodiment, a layer of bio gel may be applied on a lower surface of the drug delivery unit 1104 for adhering the drug delivery unit 1104 to the skin of the user. The bio gel may also reduce or prevent any leakage of the drug during administration. In an embodiment, the drug delivery unit 1104 may include a first part 1112 and a second part 1114. The first part 1112 may be coupled to the band 1106. Further, the second part 1114 may be detachably coupled to the first part 1112. The first part 1112 may include the transducer, while the second part 1114 may include other components, for example, a battery (not shown in FIGS. 11A to 11E) and one or more electronic circuits (not shown in FIGS. 11A to 11E).

The band 1106 includes a first band portion 1116 and a second band portion 1118 connected to the first band portion 1116. The first band portion 1116 may be a solid band and includes multiple apertures 1120. The second band portion 1118 may be a hollow band. In an embodiment, a buckle 1122 is attached to an end of the second band portion 1118. In another embodiment, the buckle 1122 may be connected to the drug delivery unit 1104. Further, the end of the second band portion 1118 may be connected to the drug delivery unit 1104. In a further embodiment, the buckle 1122 and the second band portion 1118 may be detachably connected to the drug delivery unit 1104. The buckle 1122 may be detachably connected to the first band portion 1116 to form a loop so that the wearable device 1100 may be worn on a wrist, arm or leg of the user. Further, a band loop 1124 may be provided on the first part 1112 of the drug delivery unit 1104. The band loop 1124 may be configured to receive the first band portion 1116 when the first band portion 1116 is secured to the buckle 1122.

Figure 12A:
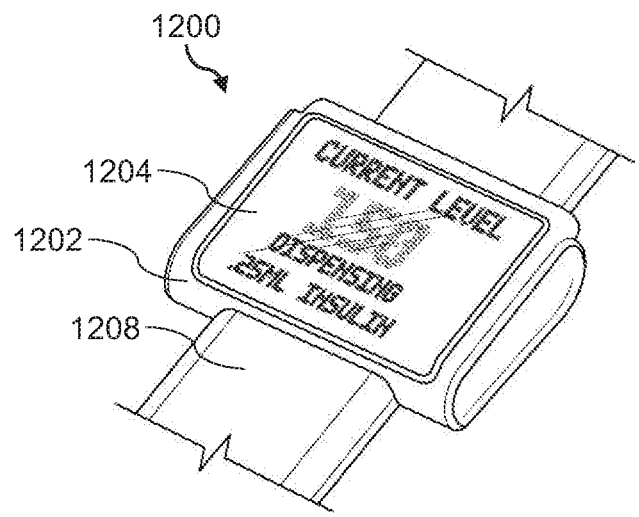
FIG. 12A is a perspective view of a processing unit that is part of a wearable device, in accordance with an embodiment of the present invention.
Figure 12B:
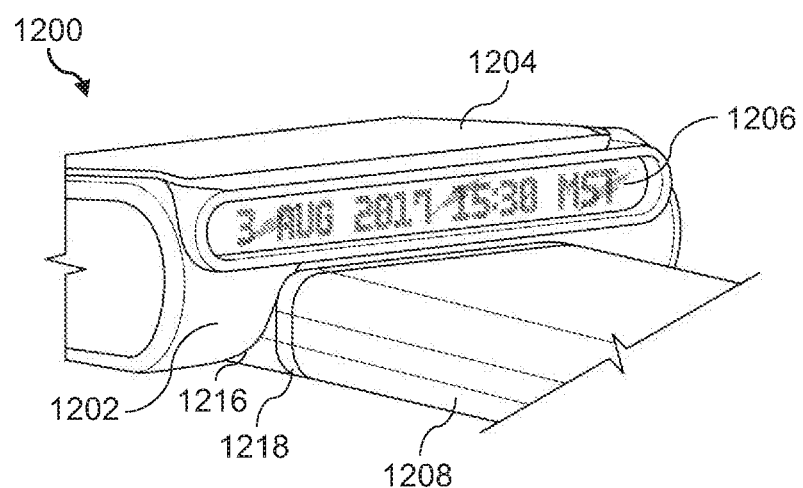
FIG. 12B is another perspective view of the processing unit of FIG. 12A.
Figure 12C:
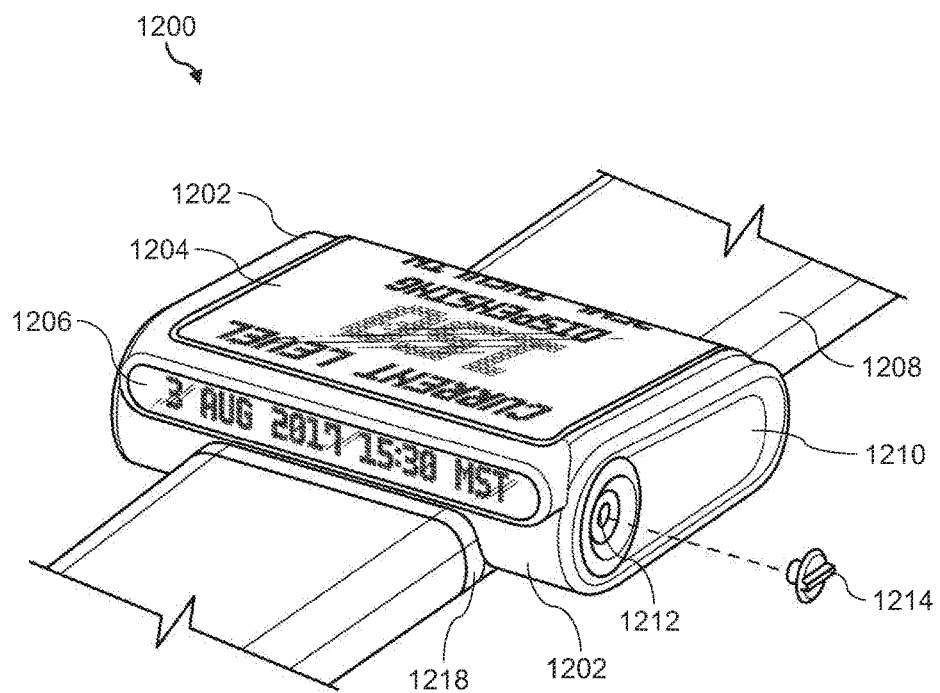
FIG. 12C is yet another perspective view of the processing unit of FIG. 12A.

FIGS. 12A to 12C illustrate various views of a processing unit 1200, according to an embodiment of the present disclosure. The processing unit 1200 may be similar to the processing unit 1102 (shown in FIG. 11A) and may be part of the wearable device 1100. The processing unit 1200 includes a housing 1202, a first screen 1204 coupled to the housing 1202 and a second screen 1206 coupled to the housing 1202. The band 1208 is connected to the processing unit 1200. In the illustrated embodiment, the processing unit 1200 is configured as a watch that can be worn on a wrist of a user using the band 1208.

In various embodiments, each of the first screen 1204 and the second screen 1206 may be a Liquid Crystal Display (LCD), a Light-Emitting Diode (LED) display, an Organic Light-Emitting Diode (OLED) display, and so forth. In further embodiments, the first screen 1204 and/or the second screen 1206 may be touchscreen displays.

The first screen 1204 may be a main display of the processing unit 1200 and located on a top surface of the housing 1202. In an embodiment, the first screen 1204 displays information about a body parameter, for example, blood glucose levels of the user. Further, the first screen 1204 displays information when a drug is being delivered to skin of the user. In an embodiment, the first screen 1204 may display a quantity of the drug that is being delivered. In the illustrated embodiment, the first screen 1204 displays that a current blood glucose level of the user is 150 and 25 ml of insulin is being dispensed.

The second screen 1206 may be a secondary display of the processing unit 1200 and located on a lateral surface of the housing 1202. In an embodiment, the second screen 1206 may display a current time and date. Further, the second screen 1206 may also display reminders generated by the processing unit 1200. In the illustrated embodiment, the second screen 1206 displays a current time, a corresponding time zone and date. Further, the second screen 1206 may allow the user to easily read the time and date without having to turn the wrist over because the second screen 1206 is located on the lateral surface of the housing 1202 facing the user.

The processing unit 1200 further includes a reservoir 1210 for storing a drug to be dispensed/administered. The reservoir 1210 may be coupled to the housing 1202 of the processing unit 1200. Further, the reservoir 1210 includes an opening 1212 that is closed by a removable cap 1214 (hereinafter referred to as "the cap 1214"). The cap 1214 can be removed from the opening 1212 to allow refilling of the reservoir 1210. After refilling, the cap 1214 is replaced.

In an embodiment, the housing 1202 of the processing unit 1200 may include a channel portion 1216 that may be mounted on the band 1208. In a further embodiment, the channel portion 1216 may be slidably mounted on the band 1208 so that a location of the processing unit 1200 may be adjustable. Further, the band 1208 may include a protruding portion 1218 that may restrict further sliding movement of the processing unit 1200. The protruding portion 1218 may also prevent the processing unit 1200 from getting detached from the band 1208 during adjustment or use.

Figure 13A:
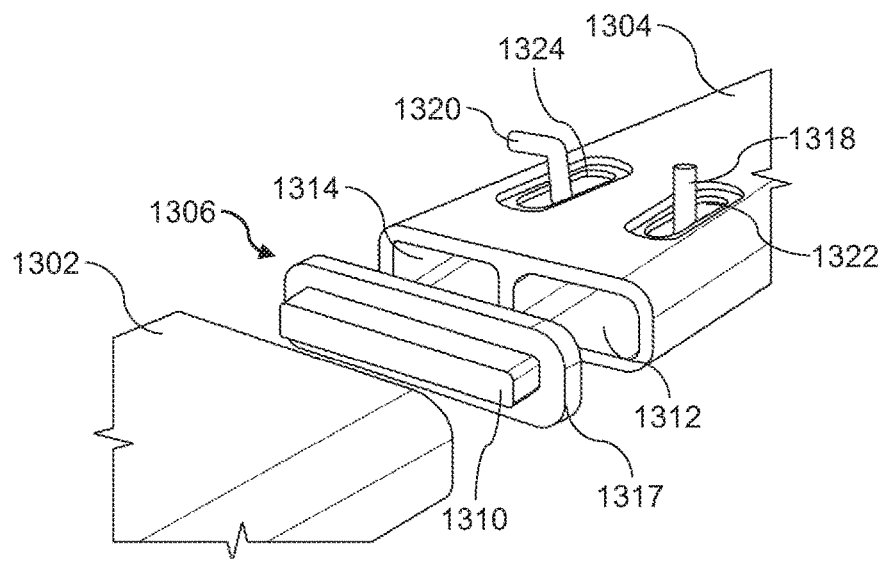
FIG. 13A is a perspective view of a band that is part of a wearable device, in accordance with an embodiment of the present invention.
Figure 13B:
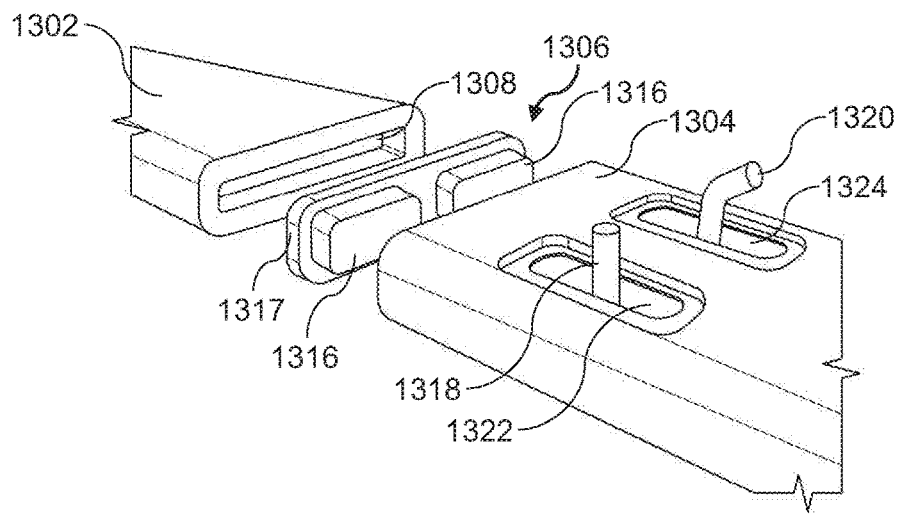
FIG. 13B is another perspective view of the band of FIG. 13A.

FIGS. 13A and 13B illustrate various views of a band 1300, according to an embodiment of the present disclosure. The band 1300 may be used with the wearable device 1100 (shown in FIGS. 11A to 11E). The processing unit 1102 and the drug delivery unit 1104 may be disposed on the band 1300. The band 1300 includes a first band portion 1302, a second band portion 1304 and a plug 1306 connecting the first band portion 1302 to the second band portion 1304. In an embodiment, the first band portion 1302 may be a solid band. Further, the second band portion 1304 may be a hollow band. The first band portion 1302 includes a recess 1308 at an end. The plug 1306 includes a first projection 1310 that is configured to be received within the recess 1308 of the first band portion 1302. The second band portion 1304 includes hollow channels 1312 and 1314 along its length. The plug 1306 includes two second projections 1316 opposite to the first projection 1310. The second projections 1316 are configured to be received in the respective hollow channels 1312 and 1314 of the second band portion 1304. The plug 1306 may seal the hollow channels 1312 and 1314 of the second band portion 1304. Further, the plug 1306 connects the first band portion 1302 to the second band portion 1304 when the first projection 1310 is received in the recess 1308 and the second projections 1316 are received in the respective hollow channels 1312 and 1314. Upon assembly of the band 1300, an outer surface 1317 of the plug 1306 may be disposed between the first and second band portions 1302, 1304, and may protrude from the band 1300. In an embodiment, the plug 1306 may be made of a suitable material or the outer surface 1317 may include a suitable coating in order to enhance an aesthetic appeal of the wearable device 1100.

In an embodiment, the processing unit 1102 may be slidably mounted on the band 1300 via one or more tracks (not shown). Therefore, a distance between the processing unit 1102 and the drug delivery unit 1104 may be adjustable, for example, in accordance with different wrist sizes of users. The user may reposition the processing unit 1102 on the band 1300 so that an optimum distance between the processing unit 1102 and the drug delivery unit 1104 is achieved. The optimum distance may allow the processing unit 1102 to be positioned at a suitable location on the dorsal side of the wrist. Further, the optimum distance may allow the drug delivery unit 1104 to be positioned at a desired location on the ventral side of the wrist. Positioning of the drug delivery unit 1104 at the desired location may be essential for proper functioning of the wearable device 1100.

A electrical cable 1318 (hereinafter referred to as "the cable 1318") may pass through the hollow channel 1312, while a drug tube 1320 may pass through the hollow channel 1314. The cable 1318 may include one or more wires. In an embodiment, the cable 1318 may electrically connect the signal generator of the processing unit 1102 with the transducer of the drug delivery unit 1104. In another embodiment, the cable 1318 may act as a communication interface between the processor of the processing unit 1102 and the transducer of the drug delivery unit 1104. In a further embodiment, the cable 1318 may relay power from the battery of the drug delivery unit 1104 to one or more components of the processing unit 1102.

In an embodiment, the drug tube 1320 may be a hollow tube configured to deliver the drug from the reservoir of the processing unit 1102 to the transducer of the drug delivery unit 1104. In another embodiment, the drug tube 1320 may be configured to deliver the drug from an outlet of the pump of the processing unit 1102 to the transducer of the drug delivery unit 1104.

The second band portion 1304 may further include two upper openings 1322 and 1324 for the cable 1318 and the drug tube 1320, respectively. The upper openings 1322 ad 1324 may allow the cable 1318 and the drug tube 1320 to extend from a top surface of the second band portion 1304. This may enable the cable 1318 and the drug tube 1320 to be connected with appropriate components of the processing unit 1102 which is disposed on a top surface of the band 1300.

In an embodiment, the outer surface 1317 of the plug 1306 may protrude from the band 1300 to restrict further sliding movement of the processing unit 1102 relative to the band 1300. The location of the outer surface 1317 may correspond to a maximum possible distance between the processing unit 1102 and the drug delivery unit 1104. The maximum possible distance may be based on a length of the cable 1318 and/or the drug tube 1320. The outer surface 1317 may also prevent the processing unit 1102 from getting detached from the band 1300 during adjustment or use.

Figure 14:
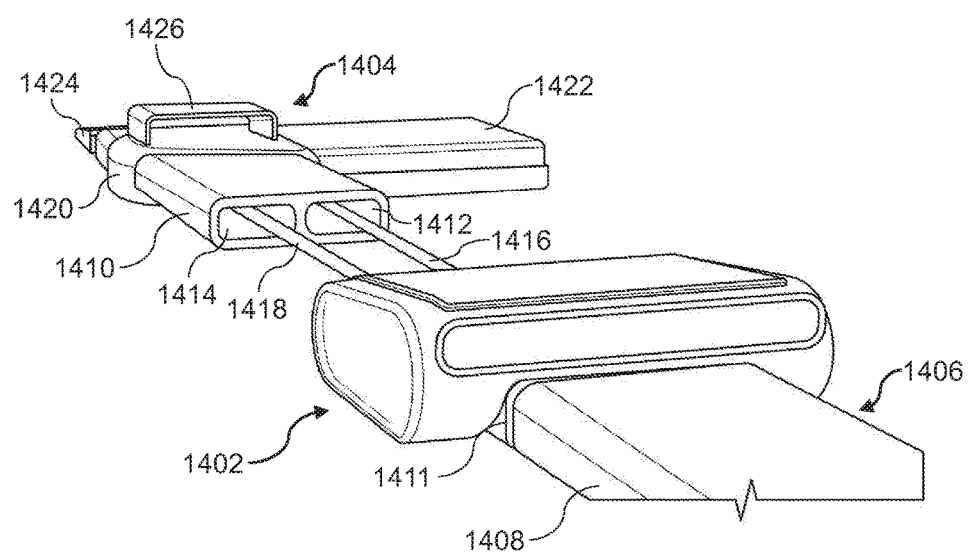
FIG. 14 is a partial perspective view of a wearable device for drug delivery, in accordance with an embodiment of the present invention.

FIG. 14 illustrates a partial view of a wearable device 1400 for drug delivery, according to an embodiment of the present disclosure. The wearable device includes a processing unit 1402, a drug delivery unit 1404 and a band 1406 for securing the wearable device 1400 to a wrist of a user. The processing unit 1402 may be similar to the processing unit 1102 of FIG. 11A. Further, the drug delivery unit 1404 may be similar to the drug delivery unit 1104 of FIG. 11A. Moreover, the band 1406 may be similar to the band 1106 of FIG. 11A. The band 1406 includes a first band portion 1408 and a second band portion 1410. In an embodiment, a plug 1411 may connect the first band portion 1408 to the second band portion 1410. For illustration purpose, a cutaway view of the second band portion 1410 is shown in FIG. 14. The second band portion 1410 includes two hollow channels 1412 and 1414 for receiving a cable 1416 and a drug tube 1418, respectively. The cable 1416 may be configured to transport electric signals and/or data signals between the processing unit 1402 and the drug delivery unit 1404. The cable 1416 may include one or more wires. Further, the drug tube 1418 may be configured to transport a drug from the processing unit 1402 to the drug delivery unit 1404. The hollow channels 1412 and 1414 may be molded into the second band portion 1410. Since the hollow channels 1412 and 1414 are isolated from each other, the cable 1416 may be protected from any leakage of the drug from the drug tube 1418. Further, the hollow channels 1412 and 1414 may provide adequate volume for movements of the cable 1416 and the drug tube 1418, respectively. Such movements of the cable 1416 and the drug tube 1418 may be caused by the activity of the user.

As illustrated in FIG. 14, the drug delivery unit 1404 includes a first part 1420 and a second part 1422. The second band portion 1410 may be connected to an end of the first part 1420. Further, a buckle 1424 is connected to another end of the first part 1420. The buckle 1424 may be detachably secured to the first band portion 1408 to form a loop so that the wearable device 1400 may be worn on a wrist of the user. The first part 1420 of the drug delivery unit 1404 may include a transducer (not shown in FIG. 14), for example, a sonic plate. The first part 1420 may also include a band loop 1426. The band loop 1426 may be configured to receive the first band portion 1408 when the first band portion 1408 is secured to the buckle 1424. The second part 1422 of the drug delivery unit 1404 may include a battery (not shown in FIG. 14) and one or more electronic circuits (not shown in FIG. 14). In an embodiment, the cable 1416 may also relay power from the battery of the drug delivery unit 1404 to one or more components of the processing unit 1402.

Figure 15:
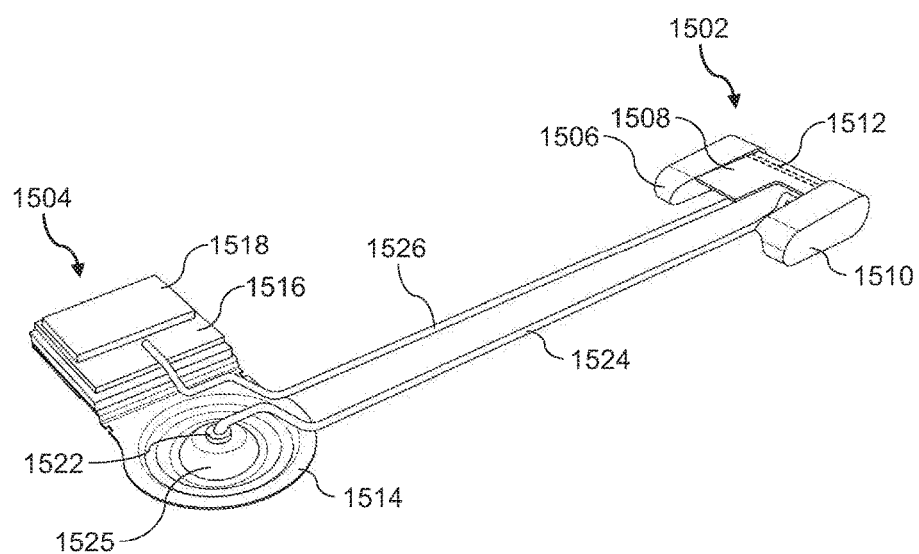
FIG. 15 is a perspective view of a wearable device for drug delivery with certain components omitted, in accordance with an embodiment of the present invention.

FIG. 15 illustrates various internal components of a wearable device 1500 for drug delivery, according to an embodiment of the present disclosure. The wearable device 1500 may be similar to the wearable device 1100 of FIG. 11A. Some external components of the wearable device 1500 (for example, housings, casings, bands etc.) have not been show for clarity.

The wearable device 1500 includes a processing unit 1502 and a drug delivery unit 1504. The processing unit 1502 may be similar to the processing unit 1102 of FIG. 11A. Further, the drug delivery unit 1504 may be similar to the drug delivery unit 1104 of FIG. 11A.

The processing unit 1502 includes a reservoir 1506, a first PCB board 1508 and a pump 1510. In an embodiment, the reservoir 1506, the first PCB board 1508 and the pump 1510 may be at least partially enclosed by a housing similar to the housing 1202 shown in FIG. 12A. The reservoir 1506 may store a drug, for example, insulin. The first PCB board 1508 may include various electrical components (not shown), for example, a processor and a signal generator. In an embodiment, one or more sensors may be communicably coupled to the first PCB board 1508. The one or more sensors may be configured to determine a body parameter of a user. The body parameter may be blood glucose levels. The first PCB board 1508 and the pump 1510 may be communicably coupled to each other. The pump 1510 may be configured to dispense a specific quantity of the drug based on control instructions from the first PCB board 1508. Further, an inlet tube 1512 (shown by broken lines) may fluidically communicate the reservoir 1506 with an inlet of the pump 1510. In an embodiment, the pump 1510 may be micropump.

The drug delivery unit 1504 includes a transducer 1514, a second PCB board 1516, a battery 1518 and a tube holder 1522. The battery 1518 and the transducer 1514 may be communicably coupled to the second PCB board 1516 via respective interfaces. In an embodiment, the transducer 1514 may be housed within a first part of the drug delivery unit 1504. The first part of the drug delivery unit 1504 may be similar to the first part 1112 shown in FIG. 11A. Further, the second PCB board 1516 and the battery 1518 may be housed within a second part of the drug delivery unit 1504. The second part of the drug delivery unit 1504 may be similar to the second part 1114 shown in FIG. 11A. The battery 1518 may be a lithium-ion battery, a nickel-cadmium battery, and the like. Further, the battery 1518 may power various components of the wearable device 1500.

In an embodiment, the transducer 1514 may be an ultrasonic transducer that generates ultrasonic waves based on control signals received from the second PCB board 1516. In the illustrated embodiment, the transducer 1514 is a sonic plate. The transducer 1514 is configured to receive a quantity of the drug from the pump 1510. A drug tube 1524 is configured to transport the drug from an outlet of the pump 1510 to the transducer 1514. The tube holder 1522 may retain the drug tube 1524 at an intake opening of the transducer 1514. Further, the tube holder 1522 may prevent any leakage of the drug from the intake opening of the transducer 1514. In an embodiment, the tube holder 1522 may be a disc with a hole for receiving the drug tube 1524. In an embodiment, the transducer 1514 may include a raised portion 1525. The raised portion 1525 may have a curvilinear shape. The raised portion 1525 may define a chamber (not shown in FIG. 15) between the transducer 1514 and skin of the user. The raised portion 1525 also includes the intake opening for receiving the drug from the drug tube 1524. The drug is received within the chamber.

In an embodiment, the second PCB board 1516 may control charging/discharging of the battery 1518. In a further embodiment, the second PCB board 1516 may control the transducer 1514 via control signals. In an embodiment, the second PCB board 1516 may include various electronic components, for example, a processor (not shown), a signal generator (not shown) and a power control circuit (not shown). A cable 1526 may be connected to the first PCB board 1508 and the second PCB board 1516. The cable 1526 may include one or more wires. In an embodiment, the cable 1526 may transport electric signals and/or data signals between the first PCB board 1508 and the second PCB board 1516. In a further embodiment, the cable 1526 may also relay power from the battery 1518 to the first PCB board 1508.

In an embodiment, the first PCB board 1508 may monitor blood glucose levels of the user based on signals received from the one or more sensors. Further, the first PCB board 1508 may determine a quantity of drug to be administered to the user based on the blood glucose levels. The first PCB board 1508 may transmit control instructions to the pump 1510 based on the determined quantity of the drug. The pump 1510 may draw the determined quantity of the drug from the reservoir 1506 via the inlet tube 1512. The pump 1510 may dispense the determined quantity of the drug to the transducer 1514 via the drug tube 1524.

In an embodiment, the first PCB board 1508 may transmit control instructions, via the cable 1526, to the second PCB board 1516 indicative of the determined quantity of the drug that is to be administered to the user. The second PCB board 1516 may transmit control signals to the transducer 1514 based on the control instructions received from the first PCB board 1508. The transducer 1514 may generate ultrasonic vibrations so that the drug received in the chamber may be transdermally administered into the bloodstream of the user through pores in the skin. The first PCB board 1508 may continue to monitor the blood glucose levels and dispense additional drug if required.

Figure 16:
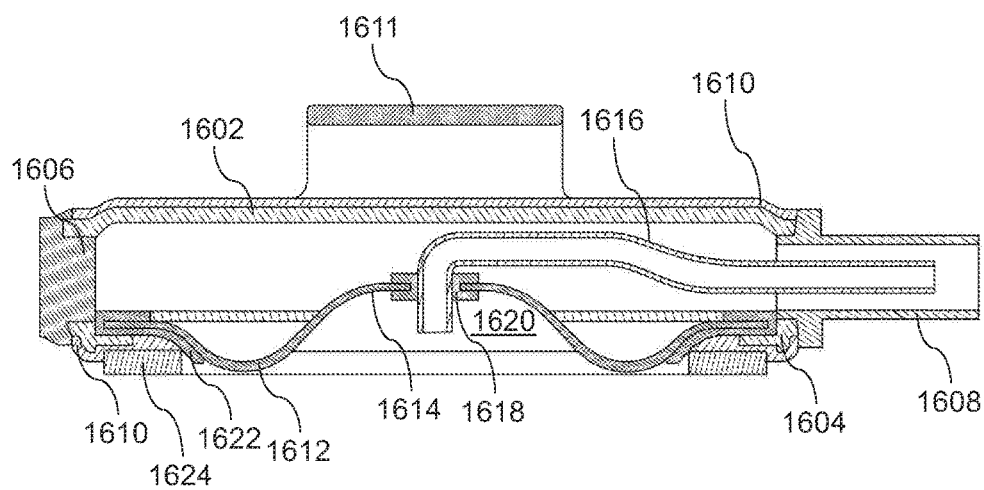
FIG. 16 is a sectional view of a drug delivery unit that is part of a wearable device, in accordance with an embodiment of the present invention.

FIG. 16 illustrates a sectional view of a drug delivery unit 1600, in accordance with an embodiment of the present disclosure. The drug delivery unit 1600 may be used with the wearable device 1100 shown in FIG. 11A. The drug delivery unit 1600 includes an upper case 1602 and a lower case 1604. A buckle cap 1606 may be coupled to the upper and lower cases 1602, 1604 at a first end of the drug delivery unit 1600. Further, a band 1608 may be coupled to the upper and lower cases 1602, 1604 at a second end of the drug delivery unit 1600. The buckle cap 1606 may be connected to a buckle (not shown in FIG. 16). The buckle in cooperation with the band 1608 may detachably secure the drug delivery unit 1600 to a wrist of a user. The buckle cap 1606 and the band 1608 may be secured to the upper and lower cases 1602, 1604 by various methods, for example, but not limited to, adhesives, mechanical joints, and so forth. Further, the upper case 1602 may be coupled to the lower case 1604 by various methods, for example, but not limited to, adhesives, mechanical joints, and so forth. In an embodiment, the buckle cap 1606 and the band 1608 may be detachably coupled to the drug delivery unit 1600.

The drug delivery unit 1600 further includes an outer silicon layer 1610 provided on the upper case 1602 and the lower case 1604. The outer silicon layer 1610 may be a silicone coating or film. The outer silicon layer 1610 may act as a seal that prevents ingress of external elements (for example, moisture, dust etc.) into the drug delivery unit 1600. Further, the outer silicon layer 1610 may also protect the upper case 1602 and the lower case 1604 from external elements. The drug delivery unit 1600 also includes a band loop 1611 on an upper surface. The band loop 1611 may be configured to receive the band 1608 when the band 1608 is secured to the buckle.

The drug delivery unit 1600 also includes a transducer 1612 disposed on the lower case 1604. The transducer 1612 includes a raised portion 1614 that includes an intake opening. The raised portion 1614 may have a curvilinear shape. A tube holder 1618 may retain a drug tube 1616 at the intake opening of the transducer 1612. The drug tube 1616 may pass through the band 1608. The tube holder 1618 may have a hole to receive the drug tube 1616 therethrough. The tube holder 1618 may further includes a recess to secure the tube holder 1618 to the raised portion 1614 of the transducer 1612. The raised portion 1614 may further define a chamber 1620 between the transducer 1612 and the skin of the user. The drug tube 1616 extends into the chamber 1620. During administration of the drug, the chamber 1620 may receive a quantity of the drug from the drug tube 1616.

In an embodiment, the transducer 1612 may be a sonic plate configured to generate ultrasonic vibrations. The vibrations of the transducer 1612 may enable transdermal delivery of the drug, received within the chamber 1620, into the bloodstream of the user. Further, a silicon seal 1622 may be provided between the transducer 1612 and the lower case 1604. The silicon seal 1622 may be made of silicone. The silicon seal 1622 may isolate the drug from various electronic components (not shown in FIG. 16) of the drug delivery unit 1600. The electronic components may include, for example, the second PCB board 1516 and the battery 1518 of FIG. 15.

In an embodiment, a bio gel layer 1624 may be applied on a bottom surface of the lower case 1604. The bio gel layer 1624 may include any type of bio gel. In an embodiment, the silicon seal 1622 may act as a guide for applying the bio gel layer 1624. For example, the bio gel may be applied on the lower case 1604 in a region that is radially outward of the silicon seal 1622. The bio gel layer 1624 may be disposed between the lower case 1604 and the skin of the user. In an embodiment, the bio gel layer 1624 may help in adhering the drug delivery unit 1600 to the skin of the user. Further, the bio gel layer 1624 may act as a seal that prevents the drug in the chamber 1620 from flowing radially outwards during administration into the skin of the user.

Figure 17A:
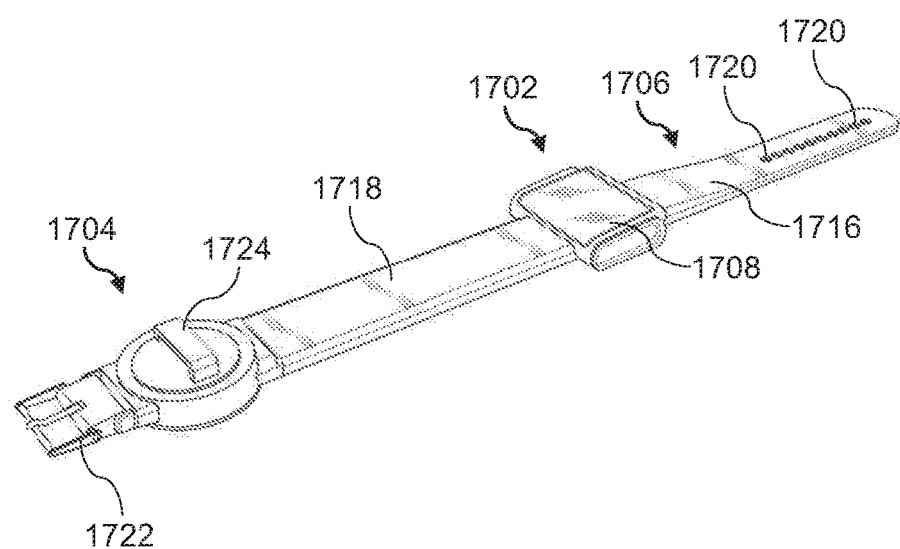
FIG. 17A is a front perspective view of a wearable device for drug delivery, in accordance with an embodiment of the present invention.
Figure 17B:
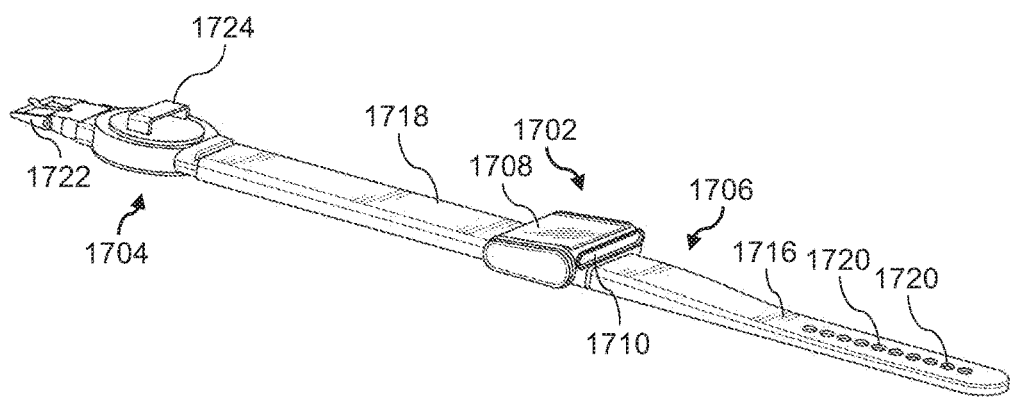
FIG. 17B is a rear perspective view of the wearable device of FIG. 17A.
Figure 17C:
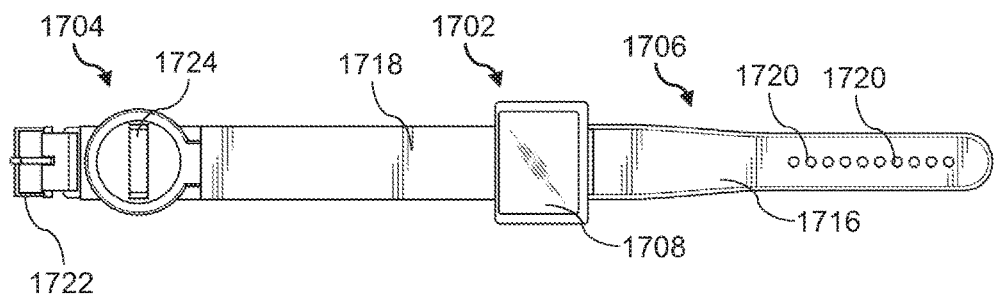
FIG. 17C is a top view of the wearable device of FIG. 17A.

FIGS. 17A to 17C illustrate various views of a wearable device 1700 for drug delivery, according to an embodiment of the present disclosure. The wearable device 1700 includes a processing unit 1702, a drug delivery unit 1704 and a band 1706 configured to be worn by a user. In the illustrated embodiment, the processing unit 1702 is shaped like a watch coupled with the band 1706. The processing unit 1702 and the drug delivery unit 1704 are further disposed on the band 1706. The processing unit 1702 includes a first screen 1708 and a second screen 1710. The processing unit 1702 may be similar to the processing unit 1102 (shown in FIG. 11A). Further, the band 1706 may be similar to the band 1106 (shown in FIG. 11A). However, the drug delivery unit 1704 may be different in configuration from the drug delivery unit 1104 (shown in FIG. 11A).

In an embodiment, the processing unit 1702 may include a sensor (not shown) that is configured to determine a body parameter of the user. The processing unit 1702 further includes a reservoir (not shown in FIGS. 17A to 17C) to store the drug (for example, insulin). The processing unit 1702 may also include a processor (not shown in FIGS. 17A to 17C) communicably coupled to the sensor. The processor receives a signal indicative of the body parameter from the sensor. The body parameter may be blood glucose level. The processor further determines a quantity of the drug to be delivered from the reservoir based on the body parameter. The processing unit also includes a signal generator (not shown in FIGS. 17A to 17C) that generates electrical signals based on control instructions received from the processor. The processor is further configured to generate indicia based on the body parameter and a user interface for displaying the indicia. The user interface may be displayed on the first screen 1708 and/or the second screen 1710. The processing unit 1702 may further include a pump (not shown in FIGS. 17A to 17C) to regulate discharge of the drug from the reservoir based on the determined quantity of the drug. In an embodiment, the processing unit 1702 may further include a battery for powering one or more components of the wearable device 1700.

In an embodiment, the drug delivery unit 1704 includes a transducer (not shown in FIGS. 17A to 17C). The transducer receives the determined quantity of the drug from the reservoir of the processing unit 1702 via a drug tube (not shown in FIGS. 17A to 17C). Further, the transducer transdermally delivers the drug to skin of the user based on an electrical signal from the signal generator. In an embodiment, the transducer may be an ultrasonic transducer. The drug delivery unit 1704 may optionally include a transdermal patch (not shown in FIGS. 17A to 17C) adhesively coupled to the skin of the user. In another embodiment, a layer of bio gel may be applied on a lower surface of the drug delivery unit 1704 for adhering the drug delivery unit 1704 to the skin of the user. The bio gel may also reduce or prevent any leakage of the drug during administration. In an embodiment, the drug delivery unit 1704 may also include other components, for example, a battery (not shown in FIGS. 17A to 17C) and one or more electronic circuits (not shown in FIGS. 17A to 17C).

In an embodiment, the transducer of the drug delivery unit 1704 may have a design that pushes the drug in a downward direction into the skin of the user. Further, the design of the transducer may be compact, thereby allowing the drug delivery unit 1704 to have a compact configuration. As a result, the wearable device 1700 may have a compact and sleek design.

In an embodiment, the band 1706 includes a first band portion 1716 and a second band portion 1718 connected to the first band portion 1716. The first band portion 1716 may be a solid band and includes multiple apertures 1720. The second band portion 1718 may be a hollow band. In an embodiment, a buckle 1722 is attached to an end of the second band portion 1718. In another embodiment, the buckle 1722 may be connected to the drug delivery unit 1704. Further, the end of the second band portion 1718 may be connected to the drug delivery unit 1704. In a further embodiment, the buckle 1722 and the second band portion 1718 may be detachably connected to the drug delivery unit 1704. The buckle 1722 may be detachably connected to the first band portion 1716 to form a loop so that the wearable device 1700 may be worn on a wrist of the user. Further, a band loop 1724 may be provided on the drug delivery unit 1704. The band loop 1724 may be configured to receive the first band portion 1716 when the first band portion 1716 is secured to the buckle 1722.

Figure 18A:
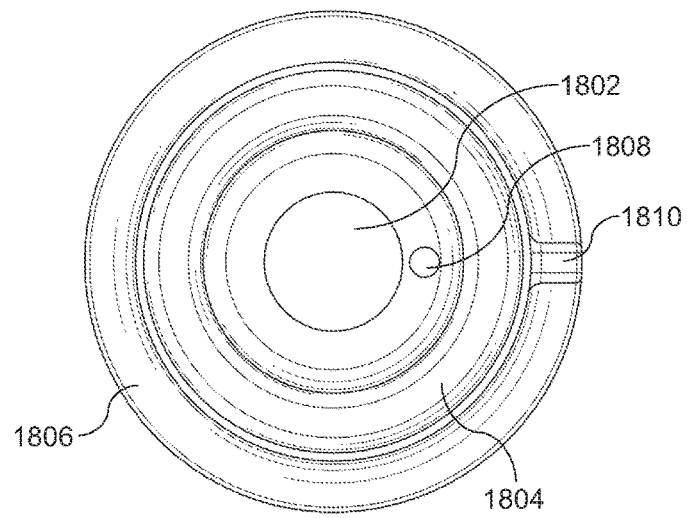
FIG. 18A is a bottom view of a transducer for use with a wearable device, in accordance with an embodiment of the present invention.
Figure 18B:
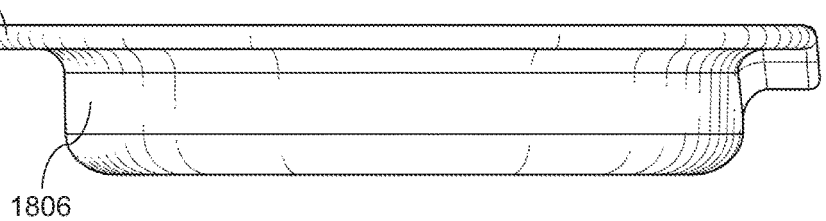
FIG. 18B is a side view of the transducer of FIG. 18A.

FIGS. 18A and 18B illustrate various views of a transducer 1800, according to an embodiment of the present disclosure. The transducer 1800 may be used in the drug delivery unit 1704 of the wearable device 1700 (shown in FIGS. 17A to 17C). In an embodiment, the transducer 1800 may have a design that pushes the drug in a downward direction into skin of a user. Further, the design of the transducer 1800 may be compact, thereby allowing the drug delivery unit 1704 to have a compact configuration. As a result, the wearable device 1700 may have a compact and sleek design.

The transducer 1800 includes a driver portion 1802, a director portion 1804 and a plate portion 1806. In an embodiment, the transducer 1800 may be a sonic plate configured to generate ultrasonic vibrations. Further, the driver portion 1802 may be a sonic driver configured to receive electric signals from a signal generator and generate ultrasonic vibrations based on the received electric signals. The transducer 1800 further includes a hole 1808 configured to receive a drug tube (not shown in FIGS. 18A and 18B) therethrough. The drug tube may deliver a drug (for example, insulin) to the transducer 1800. In an embodiment, the transducer 1800 may have define a chamber to receive the drug therein. The director portion 1804 may be a sonic director configured to direct the ultrasonic vibrations so that the drug is pushed downwards into the skin of the user. In an embodiment, the plate portion 1806 may be a metal plate configured to retain the transducer 1800 within the drug delivery unit 1704. Specifically, the plate portion 1806 may include a flange 1812 for securing the transducer 1800 to the drug delivery unit 1704. The plate portion 1806 may further include an opening 1810 configured to receive the drug tube.

Figure 19A:
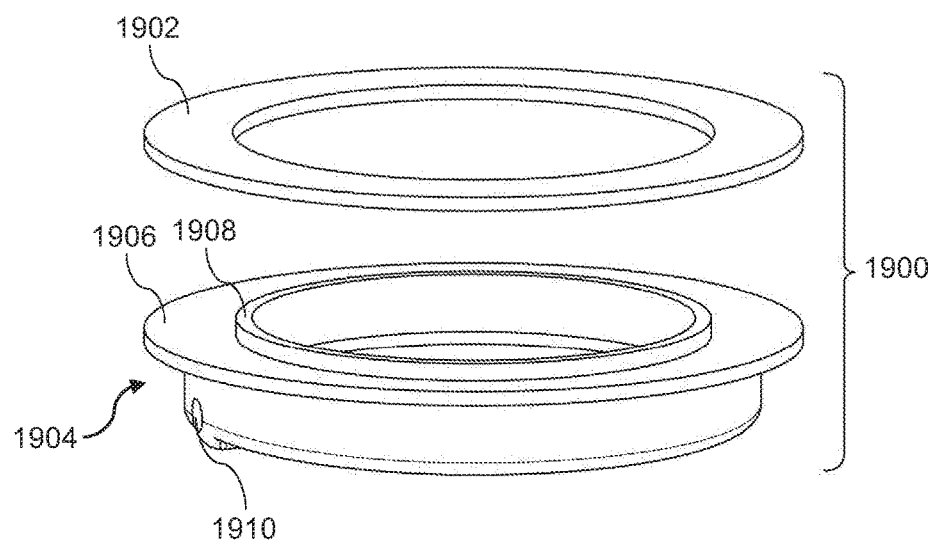
FIG. 19A is an exploded view of a sealing system for use with a wearable device, in accordance with an embodiment of the present invention.
Figure 19B:
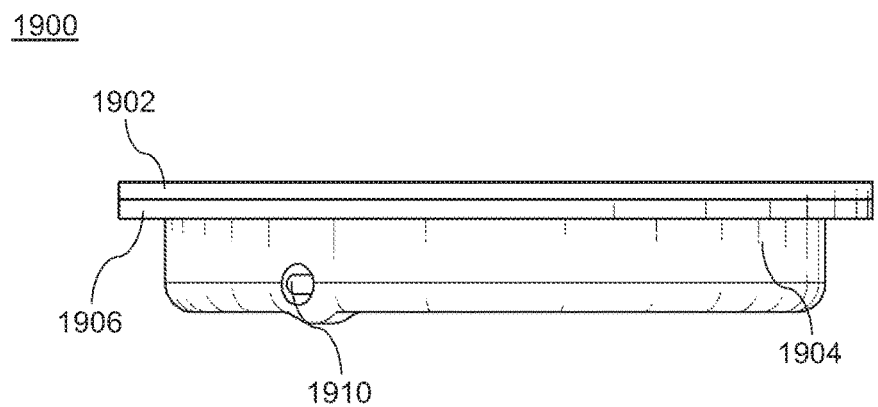
FIG. 19B is an assembled view of the sealing system of FIG. 19A.

FIGS. 19A and 19B illustrate different views of a sealing system 1900, according to an embodiment of the present disclosure. The sealing system 1900 may be used with the drug delivery unit 1704 (shown in FIGS. 17A to 17C). The sealing system 1900 includes a bio gel layer 1902 and a silicon seal 1904. The bio gel layer 1902 may be shaped like a ring. The silicon seal 1904 may include a flange portion 1906. The bio gel layer 1902 may be placed on the flange portion 1906. The silicon seal 1904 also includes a protruding portion 1908 extending from the flange portion 1906. The bio gel layer 1902 may be placed around the protruding portion 1908. The protruding portion 1908 may therefore act as a guide for applying the bio gel layer 1902. Further, the silicon seal 1904 may act as a bracket for the bio gel layer 1902. The silicon seal 1904 also includes an aperture 1910.

In an embodiment, the silicon seal 1904 may be made of silicone. The silicon seal 1904 may act as a seal for a transducer of the drug delivery unit 1704. In an embodiment, the silicon seal 1904 may act as a seal for the transducer 1800 (shown in FIGS. 18A and 18B). In a further embodiment, the silicon seal 1904 may be attached to the flange 1812 of the transducer 1800. In another embodiment, the aperture 1910 of the silicon seal 1904 may be aligned with the opening 1810 of the transducer 1800 to allow a drug tube to pass therethrough.

In an embodiment, the bio gel layer 1902 may be made of bio gel. The bio gel layer 1902 may stick to the transducer 1800, the silicon seal 1904 and/or skin of a user. The bio gel layer 1902 may act as a seal that allows a drug to be pushed into the skin of the user, while preventing ingress of foreign material (for example, dust, moisture etc.).

Figure 20:
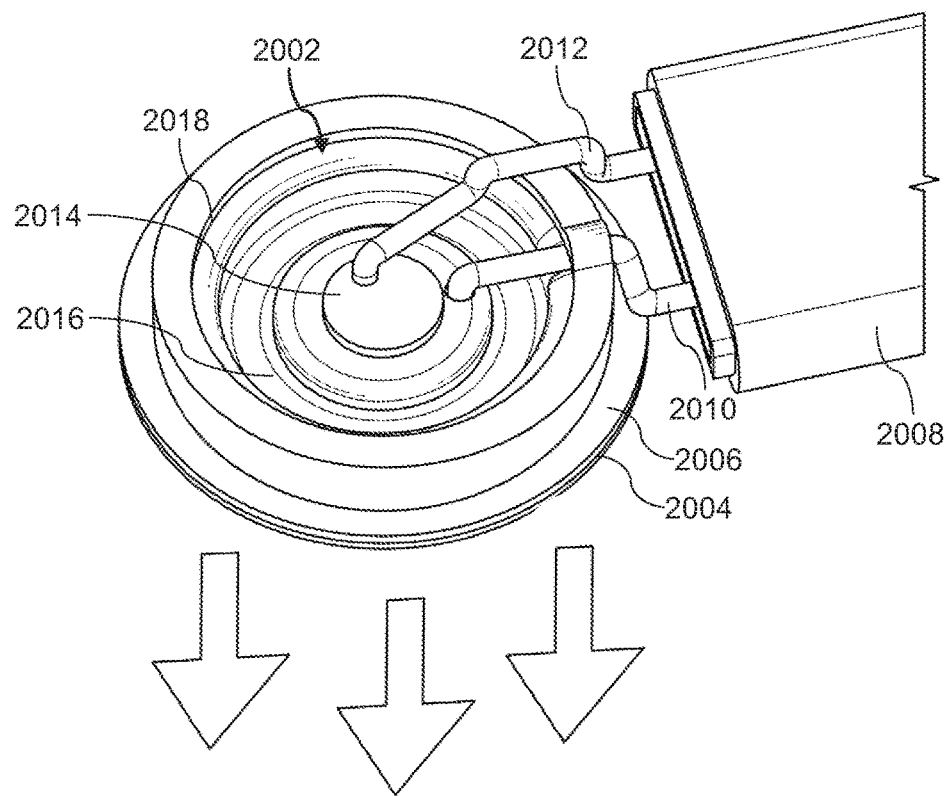
FIG. 20 is a perspective view of a drug delivery unit of a wearable device with certain components omitted, in accordance with an embodiment of the present invention.

FIG. 20 illustrates a perspective view of a delivery unit 2000, according to an embodiment of the present disclosure. One or more components (for example, a casing) of the delivery unit 2000 have been omitted in FIG. 20 for illustration purpose. The delivery unit 2000 may be similar to the delivery unit 1704 of FIG. 17A. The delivery unit 2000 includes a transducer 2002, a bio gel layer 2004 and a silicon seal 2006. The transducer 2002 may be similar to the transducer 1800 of FIGS. 18A and 18B. Further, the bio gel layer 2004 and the silicon seal 2006 may be similar to the bio gel layer 1902 and the silicon seal 1904, respectively, of FIGS. 19A and 19B.

In an embodiment, the delivery unit 2000 may be connected to a band 2008. The band 2008 may be similar to the second band portion 1718 of FIG. 17A. The band 2008 may be hollow. A drug tube 2010 and a cable 2012 may pass through the band 2008. The drug tube 2010 may be configured to transport a drug (for example, insulin) from the processing unit 1702 (shown in FIG. 17A) to the drug delivery unit 2000. Further, the cable 2012 may be configured to transmit control signals, electric power and/or data signals between the processing unit 1702 and the drug delivery unit 2000. The cable 2012 may include one or more wires. In an embodiment, the drug tube 2010 and the cable 2012 may be received within separate channels (not shown in FIG. 20) of the band 2008. Therefore, the cable 2012 may be protected against any leakage of the drug from the drug tube 2010.

As shown in FIG. 20, the transducer 2002 includes a driver portion 2014, a director portion 2016 and a plate portion 2018. The driver portion 2014, the director portion 2016 and the plate portion 2018 may be similar to the driver portion 1802, the director portion 1804 and the plate portion 1806, respectively, of FIG. 18A. The drug tube 2010 passes through an aperture (not shown in FIG. 20) of the silicon seal 2006 and an opening (not shown in FIG. 20) of the plate portion 2018. The drug tube 2010 is further received through a hole (not shown in FIG. 20) of the transducer 2002. The drug tube 2010 delivers the drug to a chamber (not shown in FIG. 20) formed between the transducer 2002 and skin of a user.

In an embodiment, the cable 2012 may pass over the silicon seal 2006 and is connected to the driver portion 1802 of the transducer 2002. The driver portion 1802 may generate ultrasonic vibrations based on electric signals received from the cable 2012. The director portion 2016 may direct the ultrasonic vibrations so that the drug is pushed downwards (indicated by arrows in FIG. 20) into the skin of the user. The bio gel layer 2004 may stick to the skin of the user and form a seal that prevents the drug from leaking outwards from the transducer 2002. Further, the bio gel layer 2004 may also prevent ingress of foreign material and safeguard the drug from contamination.

Figure 21:
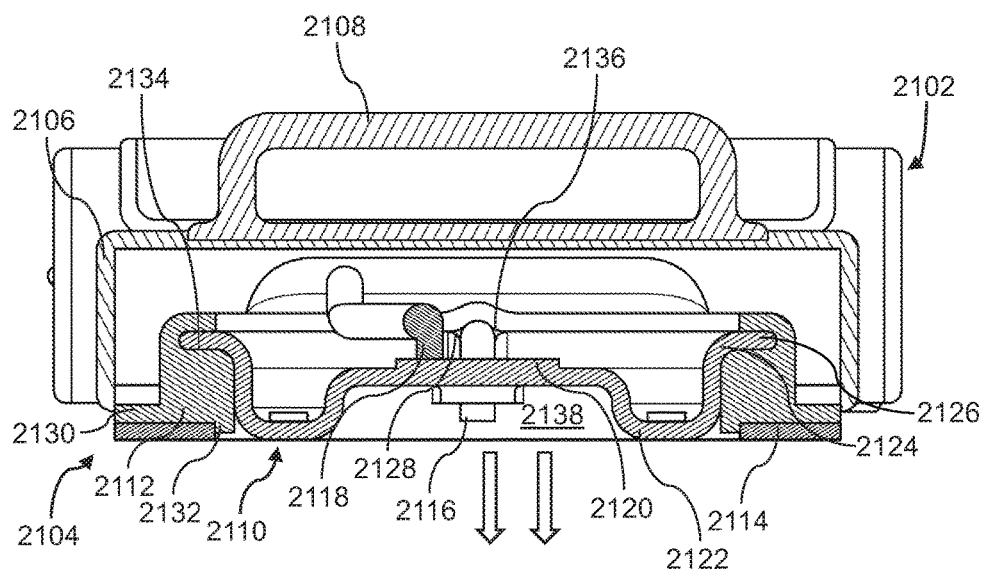
FIG. 21 is a cutaway view of a wearable device, in accordance with an embodiment of the present invention.

FIG. 21 illustrates a wearable device 2100, according to an embodiment of the present invention. The wearable device 2100 may be similar to the wearable device 1700 of FIG. 17A. The wearable device 2100 includes a processing unit 2102 and a drug delivery unit 2104. The drug delivery unit 2104 includes a casing 2106, a band loop 2108, a transducer 2110, a silicon seal 2112 and a bio gel layer 2114.

The casing 2106 may at least partially enclose various components of the drug delivery unit 2104. The casing 2106 may be further connected to a second band portion (not shown in FIG. 21) on one side and a buckle (not shown in FIG. 21) on another side. The buckle may be detachably secured to a first band portion (not shown in FIG. 21) to form a loop so that the wearable device 2100 may be worn on a wrist of a user. The band loop 2108 may be configured to receive the first band portion therethrough when the buckle is secured to the first band portion. In an embodiment, the band loop 2108 may be coupled to the casing 2106 by various methods, for example, but not limited to, mechanical joints, fasteners, adhesives, and so forth. Further, a drug tube 2116 and a cable 2118 may pass through the second band portion. The drug tube 2116 and the cable 2118 may be similar to the drug tube 2010 and the cable 2012, respectively, of FIG. 20.

In an embodiment, the transducer 2110 may be similar to the transducer 1800 of FIGS. 18A and 18B. The transducer 2110 includes a driver portion 2120, a director portion 2122 and a plate portion 2124 similar to the driver portion 1802, the director portion 1804 and the plate portion 1806, respectively, of the transducer 1800. The plate portion 2124 includes a flange 2126 and an opening 2128. Further, the silicon seal 2112 and the bio gel layer 2114 may be similar to the silicon seal 1904 and the bio gel layer 1902, respectively, of FIGS. 19A and 19B. The silicon seal 2112 includes a flange portion 2130, a protruding portion 2132, a recess 2134 and an aperture 2136. The aperture 2136 may be aligned with the opening 2128 of the transducer 2110 so that the drug tube 2116 may pass therethrough. The plate portion 2124 of the transducer 2110 may also be coupled to the silicon seal 2112. As shown in FIG. 21, the recess 2134 of the silicon seal 2112 may receive the flange 2126 of the plate portion 2124 in order to couple the transducer 2110 to the silicon seal 2112. In other embodiments, the transducer 2110 may be coupled to the silicon seal 2112 by various methods, for example, but not limited to, mechanical joints, fasteners, adhesives, and so forth. Further, the silicon seal 2112 may be coupled to the casing 2106 by various methods, for example, but not limited to, mechanical joints, fasteners, adhesives, and so forth. The silicon seal 2112 may form a seal around the transducer 2110. Further, the bio gel layer 2114 is disposed on the flange portion 2130 of the silicon seal 2112 around the protruding portion 2132. The bio gel layer 2114 may stick to skin of the user and the silicon seal 2112. The bio gel layer 2114 may therefore form a seal between the skin and the silicon seal 2112.

The drug tube 2116 may further pass through a hole (not shown in FIG. 21) of the transducer 2110. The transducer 2110 may define a chamber 2138 in which an end of the drug tube 2116 is located. The drug tube 2116 may be a hollow tube configured to transport a drug (for example, insulin) from the processing unit 2102 to the chamber 2138. Further, the cable 2118 may be connected to the driver portion 2120 of the transducer 2110. The driver portion 2120 may generate ultrasonic vibrations based on electric signals received from the cable 2118. The director portion 2122 may direct the ultrasonic vibrations so that the drug is pushed downwards (indicated by arrows in FIG. 21) into the skin of the user. The bio gel layer 2114 may prevent the drug from leaking outwards from the chamber 2138. Further, the bio gel layer 2114 may also prevent ingress of foreign material and safeguard the drug from contamination.

Figure 22:
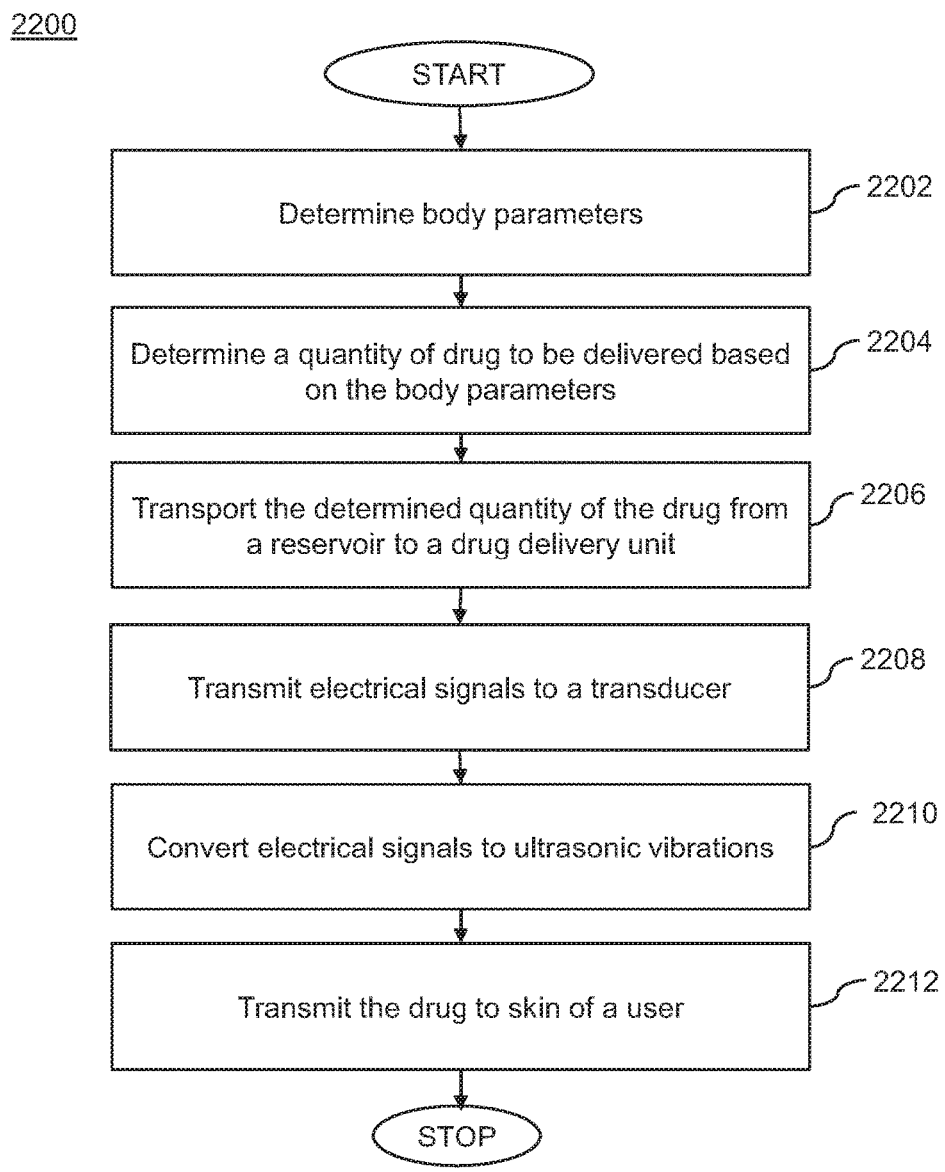
FIG. 22 illustrates a flowchart of an exemplary method to deliver a drug, in accordance with an embodiment of the present invention.

FIG. 22 illustrates a method 2200 for delivering a drug from a wearable device to the skin of the user. This flowchart is merely provided for exemplary purposes and may be implemented using the wearable devices 100, 200, 1100, 1400, 1500, 1700 or 2100 as illustrated in FIGS. 1, 2A-2B, 11A-11E, 14, 15, 17A-17C and 21. Reference will also be made to FIGS. 3A-3B, 4A-4C, and 9.

At step 2202, signals indicative of the body parameters are transmitted to the processor 902 through the bus 904. In some embodiments, the bus 904 is indicative of the wires 502 disposed within the band 500 (shown in FIG. 5). At step 2204, based on the received signals, the processor 902 determines the quantity of the drug to be discharged from the reservoir 310. Indicia pertaining to the body parameters, and the quantity of the drug to be delivered are displayed on the screen 302 through the user interface 1000 (shown in FIG. 10A). At step 2206, the processor 902 transmits control instructions to the pump 316 to enable discharge of the determined quantity of the drug from the reservoir 310. The drug is transported from the reservoir 310 to the chamber 410 through the drug tube 504.

The drug is delivered to the skin of the user through a transdermal patch 414 disposed below the chamber 410. The transdermal patch 414 is adhesively coupled to the skin. The transdermal patch 414 encapsulates drugs received from the chamber 410. The transdermal patch 414 further provides a controlled release of the drug into the bloodstream of the user through the skin. The transdermal patch 414 may include multiple layers of a porous membrane that allows the drug to pass to the skin. A coupling medium may be applied to each porous layer. The coupling medium may also be applied to the outermost porous layer of the transdermal patch 414 that faces the skin. In some embodiments, the coupling medium may be a composition of propylene glycol and water.

At step 2208, the processor 902 transmits control instructions to the signal generator 906. The signal generator 906 generates electrical signals based on the control instructions received from the processor 902. The transducer 406 may receive electrical signals from the signal generator 906 through the bus 604. In an embodiment, the electrical signals may be alternative current signals. The piezoelectric crystal in the transducer 406 undergoes rhythmic deformation due to the alternating current signals, thereby generating ultrasonic vibrations. In some embodiments, the piezoelectric crystals change size and shape when a voltage is applied. The intensity of ultrasonic vibrations may be dependent on the alternating signal transmitted and a gap between the transducer 406 and the transdermal patch 414.

At step 2210, the transducer 406 generates ultrasonic vibrations based on the electrical signals. Ultrasonic vibrations from the piezoelectric plates may facilitate in increasing widths of the pores in the skin and in the transdermal patch. At step 2212, the drug is delivered to the skin of the user from the transdermal patch. Further, the drug is transmitted to the bloodstream through pores such as, hair follicles, sweat pores and sebaceous pores on the skin of the user.

Embodiments of the present invention are directed to a wearable device for drug delivery. The wearable device is portable, lightweight, compact and may be worn by a user or patient over any body part. The wearable device includes a band or strap that may be secured in a loop over the body part. The wearable device may be secured using the buckle or other securing means, such as but not limited to, straps, Velcro or a latching mechanism. The wearable device includes a processing unit and a drug delivery unit that are disposed on skin of the user. The processing unit and the drug delivery unit may be coupled to the band. By having both the processing unit and the drug delivery unit coupled to the band, the wearable device monitors the health of the user and delivers drugs. Additionally, the wearable device also includes at least one screen that displays metrics pertaining to the body parameters and the delivery of the drug.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

A number of variations and modifications of the present invention can be used. It would be possible to provide for some features of the present invention without providing others.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present invention has been presented for purposes of illustration and description. It is not intended to limit the present invention to the form or forms disclosed herein. In the foregoing Detailed Description, for example, various features of the present invention are grouped together in one or more embodiments, configurations, or aspects for the purpose of streamlining the disclosure. The features of the embodiments, configurations, or aspects may be combined in alternate embodiments, configurations, or aspects other than those discussed above. This method of disclosure is not to be interpreted as reflecting an intention the present invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate embodiment of the present invention.

Moreover, though the description of the present invention has included description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A wearable device for delivering a drug, the wearable device comprising:
    a processing unit comprising:
        a sensor configured to determine a body parameter of a user;
        a reservoir to store the drug;
        a processor communicably coupled to the sensor, wherein the processor receives a signal indicative of the body parameter from the sensor, and wherein the processor determines a quantity of the drug to be delivered from the reservoir based on the body parameter; and
        a signal generator to generate electrical signals based on control instructions received from the processor; and
    a drug delivery unit connected to the processing unit, the drug delivery unit comprising:
        a chamber to receive the determined quantity of the drug from the reservoir; and
        a transducer connected to the chamber, wherein the transducer transdermally delivers the drug from the chamber to skin of the user based on an electrical signal received from the signal generator.

2. The wearable device of claim 1, wherein the drug delivery unit further comprises a transdermal patch adhesively coupled to the skin of the user.

3. The wearable device of claim 1, wherein the transducer further comprises a piezoelectric plate, and wherein the piezoelectric plate generates ultrasonic vibrations based on the electrical signal received from the signal generator.

4. The wearable device of claim 1, wherein the processor is further configured to:
    generate indicia based on the body parameter; and
    generate a user interface for displaying the indicia.

5. The wearable device of claim 4, wherein the processing unit further comprises a screen, and wherein the screen displays the user interface.

6. The wearable device of claim 1, further comprising a wrist band configured to be worn by a user, wherein the processing unit and the drug delivery unit are disposed on the wrist band.

7. The wearable device of claim 1, further comprising a communication interface to communicably couple the processor with the transducer.

8. The wearable device of claim 1, further comprising a drug tube, wherein the drug tube delivers the determined quantity of the drug from the reservoir to the chamber.

9. The wearable device of claim 1, wherein the processing unit further comprises a pump to regulate discharge of the drug from the reservoir based on the determined quantity of the drug.

10. A wearable device for delivering a drug, the wearable device comprising:
    a band configured to be detachably attached to a user;
    a processing unit disposed on the band, the processing unit comprising:
        a sensor configured to determine a body parameter of a user;
        a reservoir to store the drug;
        a processor communicably coupled to the sensor, wherein the processor receives a signal indicative of the body parameter from the sensor, and wherein the processor determines a quantity of the drug to be delivered from the reservoir based on the body parameter; and a signal generator to generate electrical signals based on control instructions received from the processor; and a drug delivery unit disposed on the band and connected to the processing unit, the drug delivery unit comprising:

a chamber to receive the determined quantity of the drug from the reservoir; and a transducer connected to the chamber, wherein the transducer transdermally delivers the drug from the chamber to skin of the user based on an electrical signal received from the signal generator.

11. The wearable device of claim 10, wherein the drug delivery unit further includes a transdermal patch adhesively coupled to the skin of the user.

12. The wearable device of claim 10, wherein the transducer further comprises a piezoelectric plate, and wherein the piezoelectric plate generates ultrasonic vibrations based on the electrical signal received from the signal generator.

13. The wearable device of claim 10, wherein the processing unit further comprises a pump to regulate discharge of the drug from the reservoir based on the determined quantity of the drug.

14. The wearable device of claim 10, wherein the processor is further configured to:
generate indicia based on the body parameter; and
generate a user interface for displaying the indicia.

15. The wearable device of claim 14, wherein the processing unit further comprises a screen to display the user interface.

16. The wearable device of claim 10, further comprising a communication interface disposed within the band, wherein the communication interface communicably couples the processor with the transducer.

17. A wearable device for delivering a drug, the wearable device comprising:

a band worn on a wrist of a user;
a processing unit connected to the band, the processing unit comprising:
a sensor configured to determine a body parameter of a user;
a reservoir to store the drug;
a processor communicably coupled to the sensor, wherein the processor receives a signal indicative of the body parameter from the sensor, and wherein the processor determines a quantity of the drug to be delivered from the reservoir based on the body parameter;
a pump to regulate discharge of the drug from the reservoir based on the determined quantity of the drug; and
a signal generator to generate electrical signals based on control instructions received from the processor; and
a drug delivery unit connected to the band, the drug delivery unit comprising:
a chamber to receive the determined quantity of the drug from the reservoir; and
a transducer connected to the chamber, wherein the transducer transdermally delivers the drug from the chamber to skin of the user based on an electrical signal received from the signal generator.

18. The wearable device of claim 17, wherein the processor:
generates indicia based on the body parameters; and
generates a user interface for displaying the indicia.

19. The wearable device of claim 17, further comprising a communication interface disposed within the band, wherein the communication interface communicably couples the processor with the transducer.

20. The wearable device of claim 17, further comprising a drug tube disposed within the band, wherein the drug tube delivers the determined quantity of the drug from the reservoir to the chamber.

* * * * *